(12) United States Patent
Garry et al.

(10) Patent No.: US 7,416,733 B2
(45) Date of Patent: Aug. 26, 2008

(54) FLAVIVIRUS FUSION INHIBITORS

(75) Inventors: Robert F. Garry, New Orleans, LA (US); Srikanta Dash, New Orleans, LA (US); David H. Coy, New Orleans, LA (US); Jane A McKeating, Birmingham (GB)

(73) Assignees: The Administrators of the Tulane Educational Fund, New Orleans, LA (US); The Rockefeller University, New York, NY (US)

( * ) Notice: Subject to any disclaimer, the term of this patent is extended or adjusted under 35 U.S.C. 154(b) by 324 days.

(21) Appl. No.: 10/532,480

(22) PCT Filed: Nov. 7, 2003

(86) PCT No.: PCT/US03/35666

§ 371 (c)(1),
(2), (4) Date: Apr. 22, 2005

(87) PCT Pub. No.: WO2004/044220

PCT Pub. Date: May 27, 2004

(65) Prior Publication Data

US 2005/0271677 A1 Dec. 8, 2005

Related U.S. Application Data

(60) Provisional application No. 60/424,746, filed on Nov. 8, 2002.

(51) Int. Cl.
*A61K 39/12* (2006.01)
(52) U.S. Cl. .................................. 424/218.1; 424/186.1
(58) Field of Classification Search ........................ None
See application file for complete search history.

(56) References Cited

U.S. PATENT DOCUMENTS

| | | | |
|---|---|---|---|
| 4,810,492 A | | 3/1989 | Fujita et al. |
| 5,514,539 A | * | 5/1996 | Bukh et al. ...................... 435/5 |
| 5,610,009 A | | 3/1997 | Watanabe et al. |
| 5,747,239 A | | 5/1998 | Wang et al. |
| 6,037,348 A | | 3/2000 | Colacino et al. |
| 6,117,640 A | * | 9/2000 | Srivastava et al. ............. 435/7.1 |

FOREIGN PATENT DOCUMENTS

| | | |
|---|---|---|
| EP | 0 982 402 A1 | 3/2000 |
| WO | WO 99/55366 | 11/1999 |
| WO | WO 00/09701 A1 | 2/2000 |
| WO | WO 00/75337 A1 | 12/2000 |
| WO | WO 01/51673 A1 | 7/2001 |
| WO | WO 02/072835 A1 | 9/2002 |
| WO | WO 02/081754 A1 | 10/2002 |

OTHER PUBLICATIONS

Robert F. Garry, et al., "Proteomics Computational Analysis Suggest that Hepatitis C Virus E1 and Pestivirus E2 Envelope Glycoproteins and Truncated Class II Fusion Proteins," *Virology*, 307:255-265 (2003).
Hoffman-LaRoche and Trimeris, "Roche and Trimeris Announce 24-Week Results from Second Pivotal Study of HIV Inhibitor T-20", trimeris.com/news/pr/2002/020516.html. (2002).
Richard J. Kuhn et al., "Structure of Dengue Virus: Implications for Flavivirus Organization, Maturation, and Fusion", *Cell*, 108:717-725 (2002).
R.J. Medinas et al., "C-Terminal gp40 Peptide Analogs Inhibit Feline Immunodeficiency Virus: Cell Fusion and Virus Spread", *Journal of Virology*, 76(18)9079-9086 (2002).
Julien Lescar, et al., "The Fusion Glycoprotein Shell of Semliki Forest Virus: An Icosahedral Assembly Primed for Fusogenic Activation at Endosomal pH", *Cell*, 105:137-148 (2001).
Tatiana Suárez, "Membrane Interface-Interacting Sequences within the Ectodomain of the Human Immunodeficiency Virus Type 1 Envelope Glycoprotein: Putative Role During Viral Fusion", *Journal of Virology*, 74(17):8038-8047 (2000).
M. Flint et al., "The Role of Hepatitis C Virus Glycoproteins in Infection", *Medical Virology*, 10:101-117 (2000).
Mike Flint et al., "Functional Analysis of Cell Surface-Expressed Hepatitis C Virus E2 Glycoprotein", *Journal of Virology*, 73(8):6782-6790 (1999).
Winfried Weissenhorn et al., "Crystal Structure of the Ebola Virus Membrane Fusion Subunit, GP2, from the Envelope Glycoprotein Ectodomain", *Molecular Cell*, 2:605-616 (1998).
Carl Wild et al., "A Synthetic Peptide from HIV-1 gp41 Is a Potent Inhibitor of Virus-Mediated Cell-Cell Fusion", *Aids Research and Human Retroviruses*, 9(11):1051-1053 (1993).
Carl Wild et al., "Peptides Corresponding to a Predictive α-Helical Domain of Human Immunodeficiency Virus Type 1 gp41 are Potent Inhibitors of Virus Infection", *Proc. Natl. Acad. Sci. USA*, 91:9770-9774 (1994).
William R. Gallaher, "Detection of a Fusion Peptide Sequence in the Transmembrane Protein of Human Immunodeficiency Virus", *Cell*, 50:327-328 (1987).
Volkova, T.D.; et al, "*The Protein E 98-113 Sequence as the Fusion Site of Tick-Borne Encephalitis Virus with a Cellular Membrane*", Bioorganicheskaya Khimiya (1998), vol. 24, No. 9, p. 676-681. (Abstract Only).

(Continued)

*Primary Examiner*—Stacy B Chen
(74) *Attorney, Agent, or Firm*—Howrey LLP

(57) ABSTRACT

The present invention relates to peptides and methods of inhibiting fusion between the virion envelope of Flaviviruses and membranes of the target cell, the process that delivers the viral genome into the cell cytoplasm. The invention provides for methods which employ peptides or peptide derivatives to inhibit Flavivirus:cell fusion. The present invention is based in part on the discovery that E1 envelope glycoprotein of hepaciviruses and E2 envelope glycoprotein of pestivirus have previously undescribed structures, truncated class II fusion proteins. The present invention provides peptides and methods of treatment and prophylaxis of diseases induced by Flaviviruses.

4 Claims, 9 Drawing Sheets

OTHER PUBLICATIONS

Figure 1A:
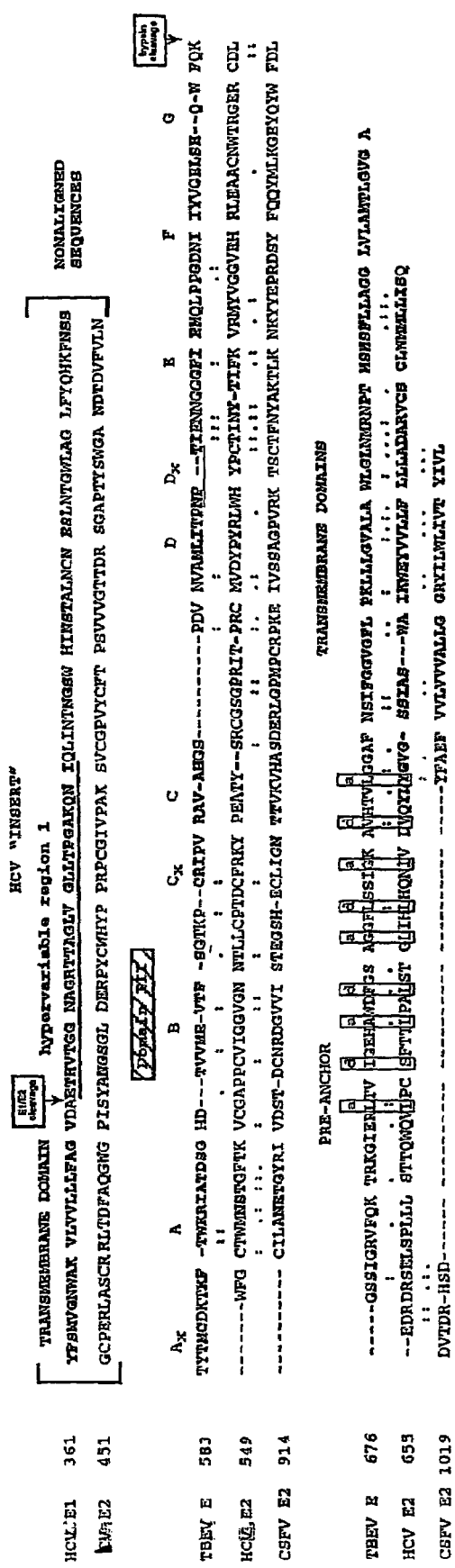

Volkova, T.D., et al, "*A Monoclonal Antibody That Recognizes The Predicted Tick-Borne Encephalitis Virus E Protein Fusion Sequence Blocks Fusion*" Archives of Virology (1999), vol. 144, p. 1035-1039.

Allison, S.L., et al, "*Mutational Evidence for an Internal Fusion Peptide in Flavivirus Envelope Protein E*", Journal of Virology (2001), vol. 75, No. 9, p. 4268-4275.

Stiasny, K., et al, "*Membrane Interactions of the Tick-Borne Encephalitis Virus Fusion Protein E at Low pH*", Journal of Virology (2002), vol. 76, No. 8, p. 3784-3790.

Crill, W.D., et al, "*Monoclonal Antibodies That Bind to Domain III of Dengue Virus E Glycoprotein Are the Most Efficient Blockers of Virus Adsorption to Vero Cells*", Journal of Virology (2001), vol. 75, No. 16, p. 7769-7773.

Bhardwaj, S., et al, "*Biophysical Characterization and Vector-Specific Antagonist Activity of Domain III of the Tick-Borne Flavivirus Envelope Protein*", Journal of Virology (2001), vol. 75, No. 8, p. 4002-4007.

Rey, F.A., et al, "*The Envelope Glycoprotein From Tick-Borne Encephalitis Virus at 2 Å Resolution*", Nature (1995), vol. 375, p. 291-298.

Hung, S., et al, "*Analysis of the Steps Involved in Dengue Virus Entry into Host Cells*", Virology (1999), vol. 257, p. 156-167.

Shai, Y., *Functional Domains within Fusion Proteins: Prospectives for Development of Peptide Inhibitors of Viral Cell Fusion*, Bioscience Reports (2000), vol. 20, No. 6, p. 535-555.

Ryman KD et al. (1997) Yellow fever virus envelope protein has two discrete type-specific neutralizing epitopes, *J. Gen. Virol.* 78:1353-1356.

http://srs.ebi.ac.uk/srsbin/cgi-bin/wgetz?-e+[uniprot-id:Q06526_9FLAV]|[uniprot-acc:Q06526_9FLAV]+-noSession Q06526_9 FLAV Jan. 11, 1996.

\* cited by examiner

Figure 1A

Figure 1B

Figure 2 tick-borne encephalitis virus envelope glycoprotein (E)

Figure 2 cont.

classic swine fever virus envelope glycoprotein 2 (E2)

A

```
TBEV prM   72                        TLAATVRKER DGSTVIRAEG KDAATQVRVE NGTCVI--LATD MGSWCDDSLS
                                                 :  ::    :   : :: :    ::          ::
CSFV E1   491  LSPYCN VTSKIGYIWY TNNCTPACLP KN-TKIIGPG KFDTNAEDGK ILHEMGGHLS-E FLLSLVVLS

TBEV prM  164  ---------- ---YECVTIDQG-E EPVDVDCFCR NVDGVYLEYG RCGKQEGSRT RRSVLIPSHA-
                              :  :    ::       :: :  :  :   ::: :     ::::
CSFV E1   561  DFAPETASAL YLIFHYV-IPQSHE EPEGCDTNQL NLT-VEL--- ---------- RTEDVIPSSVW

TBEV prM  214  -QGELTGRGHK WLEGDSLRTH LTRVEGWVWK NKLLALANVT VVWLTLESVV
                  :       :  :  ::  :    :  :    ::        ::
CSFV E1   611  NVGKYVCVRPD WWPYETKVAL LFEEAGQVVK LALRALRDLT RVW---NSAS

TBEV prM  264  TRVAVLVVLL CLAPVYA
                 :       :   : ::
CSFV E1   659  TT----AFLI CLIKVLRGQIVQGVIW LLLVTGAQ
```

FLAVIVIRUS FUSION INHIBITORS

This application is a national stage under 35 U.S.C. 371 of PCT US03/35666, filed Nov. 7, 2003, which claims the benefit of U.S. provisional application 60/424,746, filed Nov. 8, 2002, which are incorporated by reference in their entirety.

1. FIELD OF THE INVENTION

The present invention relates to peptides and methods of inhibiting cell infection and/or virion:cell fusion by members of the Flaviviridae family.

2. BACKGROUND OF THE INVENTION 2.1. Entry of enveloped animal viruses requires fusion between the viral membrane and a cellular membrane, either the plasma membrane or an internal membrane. Class I fusion proteins possess a "fusion peptide" at or near the amino terminus, a pair of extended α helices and, generally, a cluster of aromatic amino acids proximal to a hydrophobic transmembrane anchoring domain (Carr and Kim, 1993; Suarez et al., 2000; Wilson, Skehel, and Wiley, 1981). Several otherwise disparate viruses, including orthomyxoviruses, paramyxoviruses, retroviruses, arenaviruses, and filoviruses encode class I fusion proteins varying in length and sequence, but highly similar in overall structure (Gallaher, 1996; Gallaher et al., 1989). X-ray crystallography of the E glycoprotein (E-protein) of tick-borne encephalitis virus (TBEV), a member of the genus *flavivirus* of the Flaviviridae family, revealed a structure for this fusion protein distinct from other fusion proteins (Rey et al., 1995). E-protein possesses an internal fusion peptide stabilized by dicysteine linkages and three domains (I-III) comprised mostly of antiparallel β sheets. In the slightly curved rod-like configuration of the E-protein present in the virion, the fusion peptide is located at the tip of domain II, the furthest point distal from the C-terminal transmembrane anchor. Examination by Lescar and coworkers (2001) of E1, the fusion protein of the Togavirus Semliki Forest virus (SFV), revealed a remarkable fit to the scaffold of TBEV E. Recently, the E-glycoprotein of dengue virus, a medically important *flavivirus,* was also shown to have a class II structure (Kuhn et al., 2002).

2.2. The Flaviviridae family consists of three genera, *flaviviruses, hepaciviruses* and *pestiviruses.* In the United States alone, 4 million people are infected with a member of the *hepacivirus* genus, hepatitis C virus (HCV). This is four times the number infected by HIV. Each year in the US, 30-50,000 new HCV infections occur, and about 15-20,000 people die. These numbers are expected to increase dramatically. The infection is spread primarily through needle sharing among drug users, although there is some risk from accidental needle sticks, blood products before 1992, chronic blood dialysis, and frequent sexual contact. Current treatments for HCV using ribavirin and interferon cost $8,000 to $20,000 per year, and help about half of patient only partly. End stage HCV disease is the most frequent indication for liver transplants and this costs $250,000 to $300,000. Better drugs to treat HCV infection and an effective vaccine to prevent HCV infection are urgently needed. Members of the *flavivirus* genus, dengue virus, Japanese encephalitis virus, yellow fever virus, and West Nile virus, cause important human diseases world-wide. *Pestiviruses,* such as bovine viral diarrhea virus and border disease virus, cause significant veterinary illnesses.

3. SUMMARY OF THE INVENTION

Based on sequence similarities, it is likely that the E glycoproteins of other members of the *flavivirus* genus within the family Flaviviridae, including West Nile virus, are also class II fusion proteins. Analyses presented herein indicate that glycoproteins of viruses from members of the other two genera of the Flaviviridae family, *hepaciviruses* and *pestiviruses,* have previously undescribed structures. The envelope glycoprotein E1 of hepatitis C virus, a *hepacivirus,* and the envelope glycoprotein E2 of *pestiviruses* have novel structures, resembling a truncated version of a class II fusion protein. No viral protein has previously been identified with this structure. Our observations were unexpected and contrast with published studies. Hepatitis C virus encodes two envelope glycoproteins, E1 (gp35) and E2 (gp70), both with C-terminal transmembrane anchor domains. Prior studies indicated that another HCV protein, E2, has a class II structure. The structural determinations of the *hepacivirus* and *pestivirus* fusion proteins allow the identification of several heretofore unknown features of Flavivirus fusion proteins for drug and vaccine development.

Thus, the instant invention teaches that HCV envelope glycoprotein E1 has a previously unknown structure, a truncated class II fusion protein. This structure identifies regions of HCV E1 and other class II viral fusion proteins important for virus:cell fusion. This invention also teaches that peptides can be designed to inhibit viruses, including HCV and other members of the Flaviviridae family, that have fusion peptides with a class II structure.

Structural features of Flavivirus envelope glycoproteins identified herein provide surprising guidance for the development of vaccines and/or drugs to prevent or treat Flavivirus infections. Prior to the availability of X-ray structural data (Wild, Greenwell, and Matthews, 1993; Wild et al., 1994), several potent HIV-1 TM inhibitors were developed based on the Gallaher HIV-1 TM fusion protein model (Gallaher et al., 1989). DP178 (T20) peptide (FIG. 5A) has been shown to substantially reduce HIV-1 load in AIDS patients in preliminary results from phase III clinical trials. (Hoffman-La Roche and Trimeris, 2002). Peptide drugs should be relatively easy to develop, based on our structures. Once an effective peptide inhibitor is described a non-peptide drug can be developed.

More specifically, the present invention provides for methods of inhibiting viral infection by *Flaviviruses* and/or fusion between the virion envelope of *Flaviviruses* and membranes of the target cell (the process that delivers the viral genome into the cell cytoplasm). The invention is related to the discovery, as described herein, that *hepacivirus* envelope glycoprotein E1 and *pestivirus* E2 glycoprotein have novel structures. The invention provides for methods that employ peptides or peptide derivatives to inhibit *Flavivirus*:cell fusion. The present invention provides for methods of treatment and prophylaxis of diseases induced by *Flaviviruses.*

Various embodiments of the instant invention provide for pharmaceutical compositions comprising one or more peptides selected from one or more of the following groups.
A) Peptides having the sequence of any of SEQ ID NO:1 to SEQ ID NO:36;
B) Peptides homologous to any one of SEQ ID NO:1 to SEQ ID NO:36, except that they are from a different *flavivirus.*
C) Peptides that are functionally equivalent to any one of SEQ ID NO:1 to SEQ ID NO:36, wherein the functionally equivalent peptide is identical to at least one of SEQ ID NO:1 to SEQ ID NO:36 except that one or more amino acid residues has been substituted with a homologous amino acid, resulting in a functionally silent change, or one or more amino acids has been deleted.

Various aspects of this embodiment of the invention provide for compositions that comprise one or more peptides selected from the following.

A) Peptides having the amino acid sequence one or more of SEQ ID NO:1 to SEQ ID NO:36, wherein the N-terminal "Xaa" is an amino group and the C-terminal "Xaa" is a carboxyl group.
B) Peptides having the sequence of any of SEQ ID NO:1 to SEQ ID NO:36, wherein the N-terminal "Xaa" is not an amino group and/or the C-terminal "Xaa" is not a carboxyl group, wherein the N-terminal "Xaa" is selected from the group consisting of: an acetyl group, a hydrophobic group, carbobenzoxyl group, dansyl group, a t-butyloxycarbonyl group, or a macromolecular carrier group, and/or wherein the C-terminal "Xaa" is selected from the group consisting of an amido group, a hydrophobic group, t-butyloxycarbonyl group or a macromolecular group.
C) Peptides having the sequence of any of SEQ ID NO:1 to SEQ ID NO:36 except that at least one bond linking adjacent amino acid residues is a non-peptide bond.
D) Peptides having the sequence of any of SEQ ID NO:1 to SEQ ID NO:36, except that at least one amino acid residue is in the D-isomer configuration.
E) Peptides as in groups "A)" or "B)" except that at least one amino acid has been substituted for by a different amino acid (whether a conservative or non-conservative change).
F) Peptides that are a functional fragment of a peptide as set out in any of groups "A)" to "E)", above, where the peptides have at least 3 contiguous nucleotides of any one of SEQ ID NO:1 to SEQ ID NO:36.

The instant invention also provides for substantially purified antibodies that specifically react with one or more of the peptides described above.

The instant invention also provides for methods for treating or preventing viral infections in an animal where the method comprises administering to an animal or human peptides and/or antibodies as described above.

3.1. Abbreviations
HIV—human immunodeficiency virus
TBEV—tick-borne encephalitis virus
DV—dengue virus
WNV—West Nile virus
HCV—hepatitis C virus
GBV—hepatitis GB virus
CSFV—classical swine fever virus
BVDV—bovine viral diarrhea virus
BD—border disease virus
HSA—human serum albumen

4. BRIEF DESCRIPTION OF THE DRAWINGS

FIG. 1. Alignments of tick-borne encephalitis virus E, hepatitis C virus E1 and classical swine fever virus E2 glycoproteins. Panel A: Certain portions of the TBEV E (SEQ ID NO:66), HCV E1 (SEQ ID NO:67), CSFV E2 (SEQ ID NO:68) and HCV E2 (SEQ ID NO:71) polyproteins are aligned. Bracketed HCV insert sequences (HCV E1, SEQ ID NO:69; HCV E2, SEQ ID NO:70) are wrapped and do not represent an alignment comparison (FIG. 1A cont.). "(:)" refers to identical amino acids. "(.)" refers to chemically similar amino acids. Panel B: Linear arrangement of the domain structure of TBEV E as determined by Rey et al. (1995). Regions of significant sequence similarities to TBEV E in HCV E1 and E2 and CSFV E2 as determined by the PRSS3 sequence alignment program are indicated. Probabilities (p-values) are based on 1000 shuffles.

Figure 2:
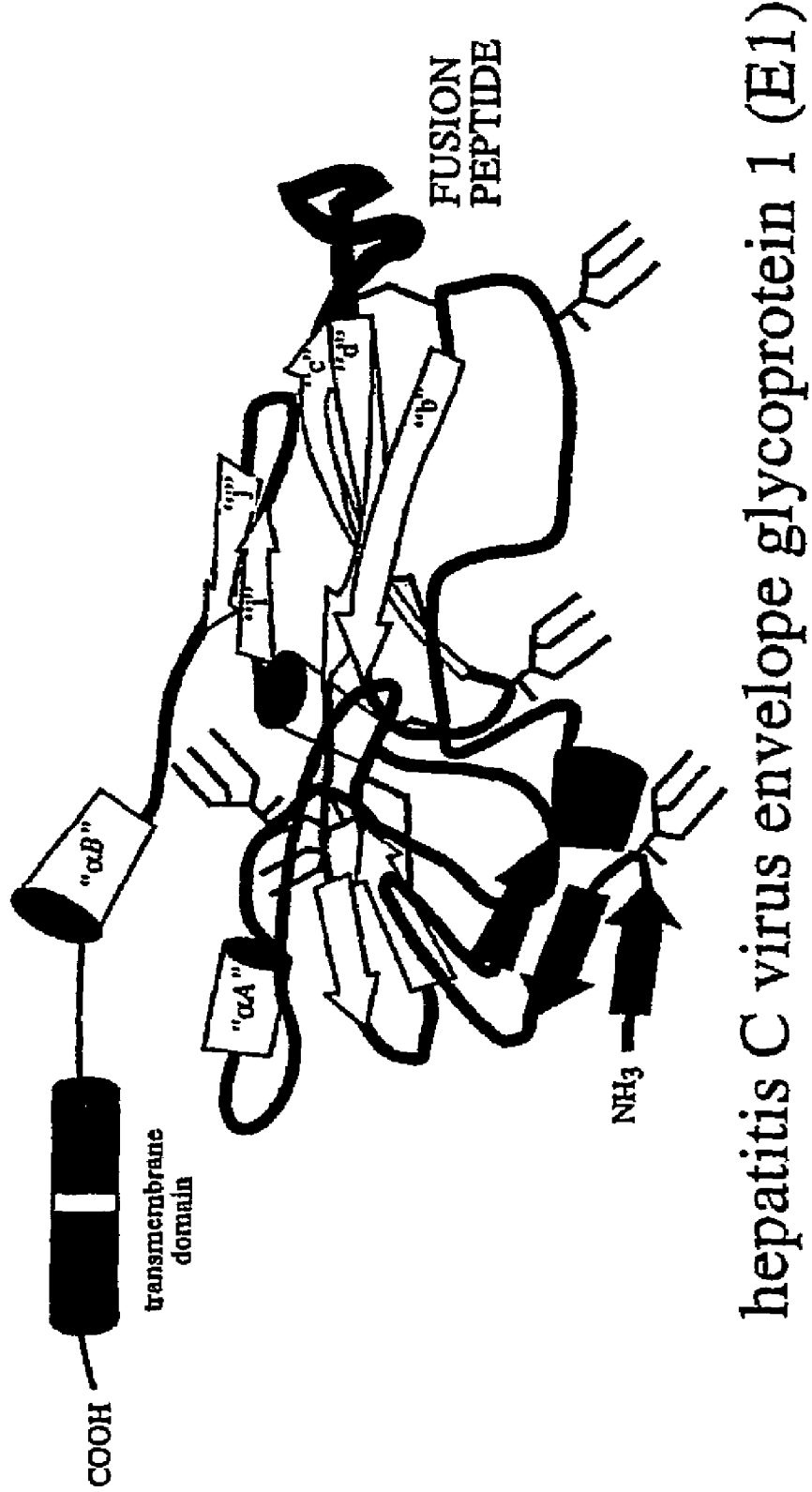

FIG. 2. Structures of *hepacivirus* E1 and *pestivirus* E2 glycoproteins. Panel A. Structure of TBEV E as determined by Rey et al. (1995) is shown schematically (traced from a RasMac molecular visualization software rendering). Panel B: Structure of HCV E1. HCV E1 sequences with similarity to TBEV E sequences are enclosed in quotation marks. Panel C: Structure of CSFV E2.

FIG. 3. Panel A: Aligned portions of the TBEV small membrane protein (prM, SEQ ID NO:72) and CSFV E1 (SEQ ID NO:73) protein. Alignments were constructed as detailed in the text. Panel B: Linear arrangement of TBEV prM and CSFV E1 with a region of sequence similarity determined by the PPSS3 algorithm indicted.

Figure 4:
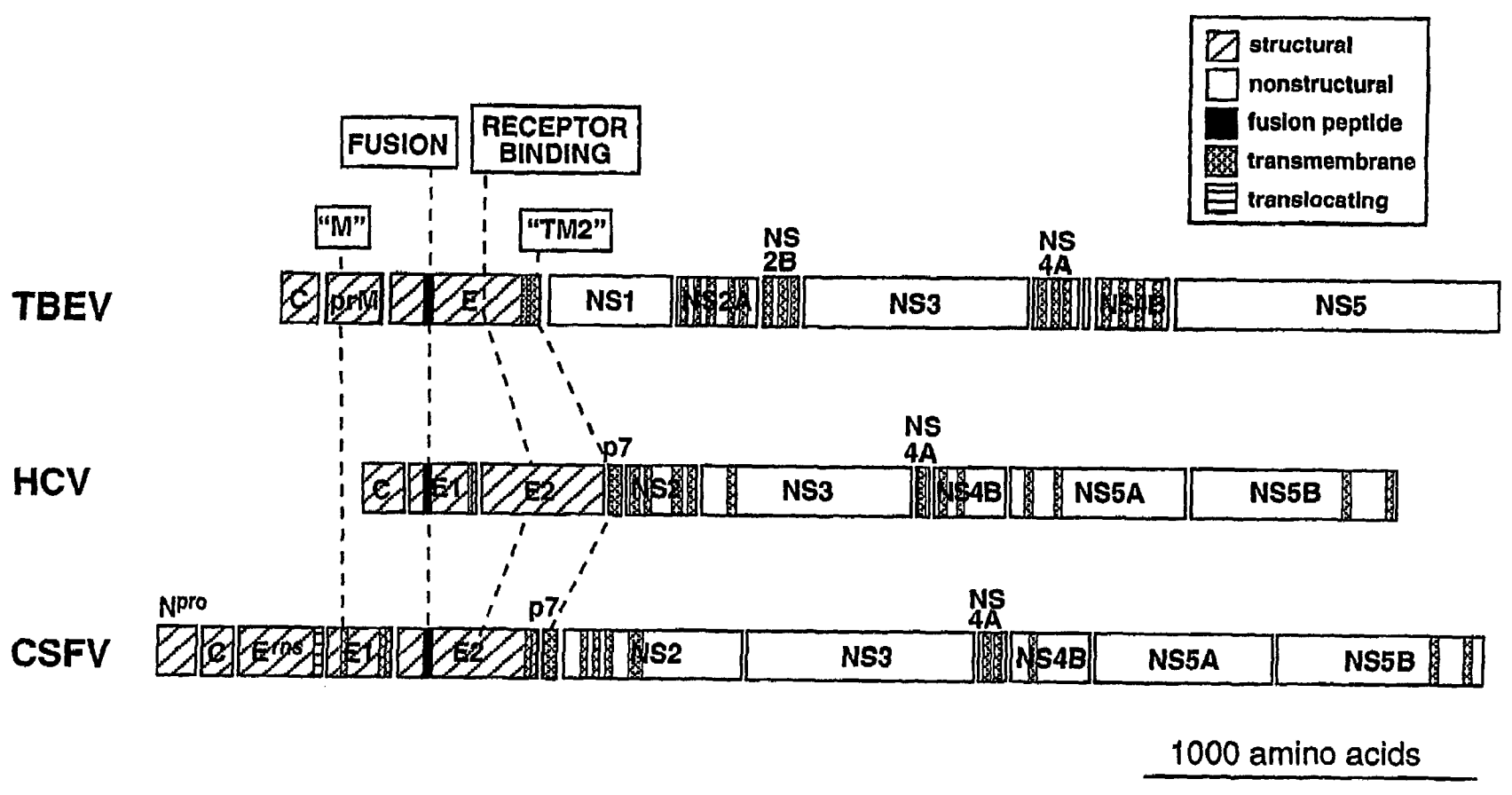

FIG. 4. Common order of proteins in Flaviviridae polyproteins. Proteins or portions of proteins with similar functions are located in similar locations along the polyproteins of members of the Flaviviridae. Hydrophobic domains were predicted using TMpred.

Figure 5:
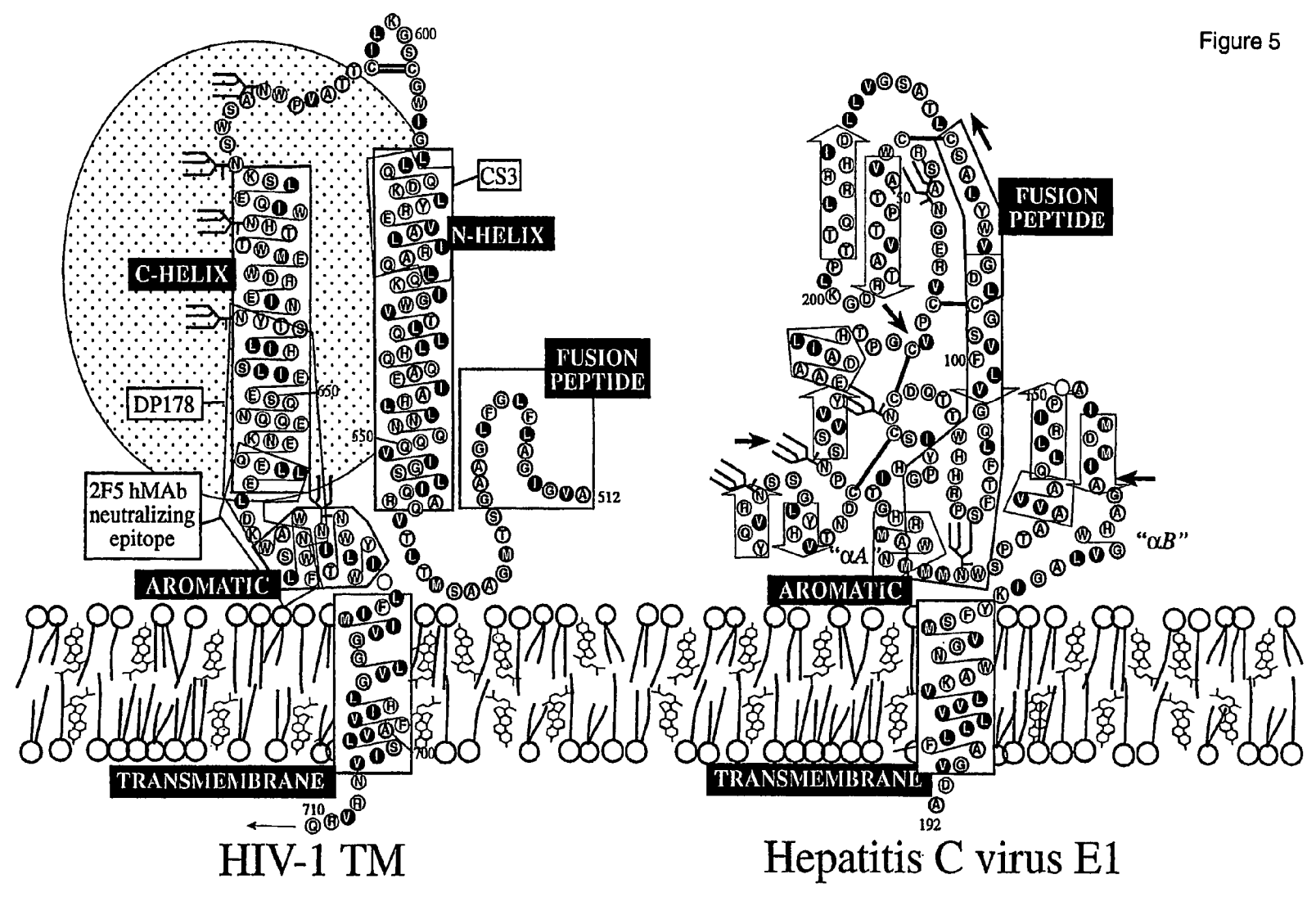

FIG. 5. Comparison of human immunodeficiency virus transmembrane glycoprotein (TM) with hepatitis C virus envelope glycoprotein 1 (E1). Presented on the left side of the figure is an updated structure of HIV-1 TM sequence (SEQ ID NO:74) from Gallaher et al. (1989) with structural motifs indicated in rainbow order. Amino acids are numbered from the beginning of the Env polyprotein. HIV-1 TM is truncated after the transmembrane domain. The precise ends of the TM N- and C-helices are unclear because of conflicting structural data. No attempt was made to align the N- and C-helices, although points of contact are solved in the coiled-coil formations. Positions of known neutralizing epitopes on TM are indicated, as well as sequences corresponding to peptides CS3 and DP178 (T20) (Qureshi et al., 1990; Wild et al., 1994) that inhibit HIV-1 infectivity. Presented on the right side of the figure is the structure of HCV E1 sequence (SEQ ID NO:75) with motifs that are shared with HIV-1 TM. Boxed arrows are predicted beta sheet structures that are similar to the indicated β sheets of TBEV E. Predicted α helical structures are outlined. Arrows denote directions that the HCV E1 structure could fold in three dimensions.

5. DETAILED DESCRIPTION OF THE INVENTION

The present invention relates to methods of inhibiting *Flavivirus* infection that comprises inhibiting the fusion between the virion envelope and a cell membrane, the process that delivers the viral genome into the cell cytoplasm. For purposes of clarity of disclosure, and not by way of limitation, the description of the present invention will be divided into the following subsections:
(i) peptides of the invention
(ii) utility of the invention

5.1. Peptides of the Invention

Any peptide or protein which inhibits the fusion between the *Flavivirus* virion envelope and a cell membrane, including those of *Flaviviruses* which infect human as well as nonhuman hosts, may be used according to the invention. In various embodiments of the invention, these inhibitors may include, but are not limited to peptides related to several membrane-interactive domains of *Flavivirus* fusion proteins.

*Flavivirus* inhibitory peptides are, according to the instant invention, identical or homologous to the amino acid sequences HCV Fusion Inhibitory Protein 1, X-YQVRNSS-GLYHVTNDCPNSSIVYEAADAIL-Z (SEQ ID NO:1); HCV Fusion Inhibitory Protein 2, X-CSALYWVGDLCGS-VFLVGQLFTFSPRRHWTTQDC-Z (SEQ ID NO:2); HCV Fusion Inhibitory Protein 3, X-SPRRHWTTQDCNC-SIYPGHITGHRMAWDMMMNWSPT-Z (SEQ ID NO:3); or HCV Fusion Inhibitory Protein 4, X-MMMN-WSPTAALLRIPQAIMDMIAGAHWGV-LAGIKYFSMVGNW-Z (SEQ ID NO:4), or portions thereof or, alternatively, to a homologous peptide sequence associated with another *Flavivirus,* including, but not limited to, HGB, DV, JEV, YFV, WNV, CSFV, BVDV, or BDV as provided below in tables 1 through 4.

As used herein the term "homologous peptide" preferably refers to similar peptides from other strains of a given virus or, alternatively from related viruses.

As used herein the term "similar peptides" refers to those peptides having at least 70% identical or chemically similar amino acids. More preferably, it refers to peptides having 75%, 80%, 85%, 90%, 95%, or greater identical and/or chemically equivalent amino acid resides.

As used herein the terms "portion thereof" refers to the peptide resulting from the removal of from one or more amino acids from either or both ends of the listed peptide, i.e. a truncated peptide. The number of amino acids removed may vary from 1-10 so long as the remaining fragment is "functional". As defined herein the term "functional fragment" refers to a fragment capable of inhibiting virus:cell fusion, inhibiting viral infectivity, capable of eliciting an antibody capable of recognizing and specifically binding to non-truncated peptide and/or interfering with *Flavivirus* envelope protein-mediated cell infection.

TABLE 1

Flavivirus fusion inhibitory peptide 1

| PROTEIN | SEQUENCE | |
|---|---|---|
| HCV E1 | X-YQVRNSSGLYHVTNDCPNSSIVYEAADAIL-Z | (SEQ ID NO:1) |
| HGB E1 | X-RVTDPDTNTTILTNCCQRNQVIYCSPSTCL-Z | (SEQ ID NO:5) |
| DV E | X-RDFVEGVSGGSWVDIVLEHGSCVTTMAKNKPTLDF-Z | (SEQ ID NO:6) |
| JEV E | X-RDFIEGASGATWVDLVLEGDSCLTIMANDKPTLDV-Z | (SEQ ID NO:7) |
| YFV E | X-RDFIEGVHGGTWVSATLEQDKCVTVMAPDKPSLDI-Z | (SEQ ID NO:8) |
| WNV E | X-RDFLEGVSGATWVDLVLEGDSCVTIMSKDKPTIDV-Z | (SEQ ID NO:9) |
| CSFV E2 | X-GQLACKEDYRYAAISSTNEIGLLGAGGLTTTWKEYN-Z | (SEQ ID NO:10) |
| BVDV E2 | X-GHLDCKPEFSYAIAKDERIGQLGAEGLTTTWKEYS-Z | (SEQ ID NO:11) |
| BDV E2 | X-GEFACREDHRYALAKTKEIGPLGAESLTTTWTDYQ-Z | (SEQ ID NO:12) |

TABLE 2

Flavivirus fusion inhibitory peptide 2

| PROTEIN | SEQUENCE | |
|---|---|---|
| HCV E1 | X-CSALYWVGDLCGSVFLVGQLFTFSPRRHWTTQDC-Z | (SEQ ID NO:2) |
| HGB E1 | X-TCDALDIGELCGACVLVGDWLVRHWLIHIDLNET-Z | (SEQ ID NO:13) |
| DV E | X-KRFVCKHSMVDRGWGNGCGLFGKGGIVTCAMFTC-Z | (SEQ ID NO:14) |
| JEV E | X-SSYVCKQGFTDRGWWGNGCGLFGKGSIDTCAKFSC-Z | (SEQ ID NO:15) |
| YFV E | X-GDNACKRTYSDRGWGNGCGLFGKGSIVACAKFTC-Z | (SEQ ID NO:16) |
| WNV E | X-PAFVCRQGVVDRGWGNGCGLFGKGSIDTCAKFAC-Z | (SEQ ID NO:17) |
| CSFV E2 | X-KGKYNTTLLNGSAFYLVCPIGWTGVIECTAVSPT-Z | (SEQ ID NO:18) |
| BVDV E2 | X-RGKFNTTLLNGPAFQMVCPIGWTGTVSCTSFNMD-Z | (SEQ ID NO:19) |
| BDV E2 | X-RGKYNATLLNGSAFQLVCPYEWTGRVECTTISKS-Z | (SEQ ID NO:20) |

TABLE 3

Flavivirus fusion inhibitory peptide 3

| PROTEIN | SEQUENCE | |
|---|---|---|
| HCV E1 | X-SPRRHWTTQDCNCSIYPGHITGHRMAWDMMMNWSPT-Z | (SEQ ID NO:3) |
| HGB E2 | X-IHIDLNETGTCYLEVPTGIDPGFLGFIGWMAGKVEA-Z | (SEQ ID NO:21) |
| DV E | X-MVLLQMEDKAWLVHRQWFLDLPLPWLPGADTQGSNW-Z | (SEQ ID NO:22) |
| JEV E | X-FYVMTVGSKSFLVHREWFHDLALPWTSPSSTAWRNR-Z | (SEQ ID NO:23) |
| YFV E | X-SYIAEMETESWIVDRQWAQDLTLPWQSGSGGVWREM-Z | (SEQ ID NO:24) |
| WNV E | X-YYVMTVGTKTFLVHREWFMDLNLPWSSAGSTVWRNR-Z | (SEQ ID NO:25) |
| CSFV E2 | X-TLRTEVVKTFRRDKPFPHRMDAVTTTVENEDLFY-Z | (SEQ ID NO:26) |
| BVDV E2 | X-TLATEVVKIYKRTKRFRSGLVATHTTIYEEDLYH-Z | (SEQ ID NO:27) |
| BDV E2 | X-TLATTVVRTYRRSKPFPHRQGAITQKNLGEDLH-Z | (SEQ ID NO:28) |

TABLE 4

Flavivirus fusion inhibitory peptide 4

| PROTEIN | SEQUENCE | |
|---|---|---|
| HCV E1 | X-MMMNWSPTAALLRIPQAIMDMIAGAHWGVLAGIKYFSMVGNW-Z | (SEQ ID NO:4) |
| HGB E1 | X-WMAGKVEAVIFLTKLASQVPYAIATMFSSVHYLAVGALIYYS-Z | (SEQ ID NO:29) |
| DV E | X-MAILGDTAWDFGSLGGVFTSIGKALHQVFGAIYGAAFSGVSW-Z | (SEQ ID NO:30) |
| JEV E | X-LAALGDTAWDFGSIGGVFNSIGKAVHQVFGGAFRTLFGGMSW-Z | (SEQ ID NO:31) |
| YFV E | X-LAVMGDTAWDFSSAGGFFTSVGKGIHTVFGSAFQGLFGGLNW-Z | (SEQ ID NO:32) |
| WNV E | X-LAALGDTAWDFGSVGGVFTSVGKAVHQVFGGAFRSLFGGMSW-Z | (SEQ ID NO:33) |
| CSFV E2 | X-QQYMLKGEYQYWFDLDVTDRHSDYFAEFVVLVVVALLGGRYI-Z | (SEQ ID NO:34) |
| BVDV E2 | X-QQYMLKGEYQYWFDLEVTDHHRDYFAESILVVVALLGGRYV-Z | (SEQ ID NO:35) |
| BDV E2 | X-QQYMLKGQYQYWFDLEVISSTHQIDLTEFIMLAVVALLGGRYV-Z | (SEQ ID NO:36) |

According to the instant invention peptides related to the *Flavivirus* fusion inhibitory peptides (FIP) preferably comprise at least three contiguous residues of the FIP peptides, or a homologous peptide, more preferably they comprise 4, 5, 6, or 7 contiguous residues. Even more preferably they comprise at least 8, 9, 10, 11, 12, 13, 14, 15, 16, 17, 18, 19, 20, 21, 22, 23, 24, 25, 26, 27, 28, 29, or 30 contiguous residues, and most preferably all residues of these sequences. As used herein the term *Flavivirus* inhibitory peptides preferably means peptides having a sequence identical to the corresponding portion of the *Flavivirus* inhibitory protein and peptides in which one or more amino acids are substituted by functionally equivalent amino acids (see infra). The term also refers to derivatives of these peptides, including but not limited to benzylated derivatives, glycosylated derivatives, and peptides which include enantiomers of naturally occurring amino acids. In other embodiments of the invention, the *Flavivirus* inhibitory peptides, related peptides or derivatives are linked to a carrier molecule such as a protein. Proteins contemplated as being useful according to this embodiment of the invention, include but are not limited to, (human serum albumen). *Flavivirus* inhibitory peptide-related peptides comprising additional amino acids are also contemplated as useful according to the invention.

Peptides may be produced from naturally occurring or recombinant viral proteins, or may be produced using standard recombinant DNA techniques (e.g. the expression of peptide by a microorganism which contains recombinant nucleic acid molecule encoding the desired peptide, under the control of a suitable transcriptional promoter, and the harvesting of desired peptide from said microorganism). Preferably, the peptides of the invention may be synthesized using any methodology known in the art, including but not limited to, Merrifield solid phase synthesis (Clark-Lewis et al., 1986, Science 231:134-139).

The FIP, or fragments or derivatives thereof, of the invention include, but are not limited to, those containing, as a primary amino acid sequences the amino acid sequence HCV Fusion Inhibitory Protein 1, X-YQVRNSSGLYHVTNDCP-NSSIVYEAADAIL-Z (SEQ ID NO:1); HCV Fusion Inhibitory Protein 2 X-CSALYWVGDLCGSVFLVGQLFTF-SPRRHWTTQDC-Z (SEQ ID NO:2); HCV Fusion Inhibitory Protein 3, X-SPRRHWTTQDCNCSIYPGHIT-GHRMAWDMMMNWSPT-Z (SEQ ID NO:3); or HCV Fusion Inhibitory Protein 4, X-MMMNWSPTAALL-RIPQAIMDMIAGAHWGVLAGIKYFSMVGNW-Z (SEQ ID NO:4), or a functional portion or functional portions thereof. Also contemplated are homologous peptide sequences associated with another *Flaviviruses,* including, but not limited to, HGB, DV, JEV, YFV, WNV, CSFV, BVDV, or BDV. Also contemplated are altered sequences (i.e. altered from any of the sequences referred to herein) in which functionally equivalent amino acid residues are substituted for residues within the sequence, resulting in a functionally silent change. For example, one or more amino acid residues within the sequence can be substituted by replacing the original amino acid with another amino acid, of a similar polarity, that acts as a functional equivalent, resulting in a functionally silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. For example, and not by way of limitation, such peptides may also comprise one or more D-amino acids. Furthermore, in any of the embodiments of the instant invention the peptide may comprise an inefficient carrier protein, or no carrier protein at all.

5.3. Utility of the Invention

The *Flavivirus* inhibitory peptides of the instant invention may be utilized to inhibit *Flavivirus* virion:cell fusion and may, accordingly, be used in the treatment of *Flavivirus* infection and also in prophylaxis against *Flavivirus* infection. The peptides of the invention may be administered to patients in any sterile, biocompatible pharmaceutical carrier, including, but not limited to, saline, buffered saline, dextrose, and water. Methods for administering peptides to patients are well known to those of skill in the art; they include, but are not limited to, intradermal, intramuscular, intraperitoneal, intravenous, subcutaneous, oral, and intranasal. In addition, it may be desirable to introduce the pharmaceutical compositions of the invention into the central nervous system by any suitable route, including intraventricular and intrathecal injection.

The instant invention provides for pharmaceutical compositions comprising *Flavivirus* inhibitory peptides, peptide fragments, or derivatives (as described supra) administered via liposomes, microparticles, or microcapsules. Various embodiments of the invention, contemplate the use of such compositions to achieve sustained release of *Flavivirus* inhibitory peptides. Other embodiments contemplate the administration of the FIP or derivatives thereof, linked to a molecular carrier (e.g. HSA).

Various embodiments of the instant invention provide for administration of the *Flavivirus* inhibitory peptides and/or antibodies specific for the these peptides to human or animal subjects who suffer from *Flavivirus* infection (e.g. dengue hemorrhagic fever, West Nile disease, hepatitis C or classical swine fever). In any embodiment the peptides and/or antibodies are typically substantially purified (as used herein the term "substantially purified" refers to a peptide, peptide analog, or antibody that is greater than about 80% pure. More preferably, "substantially purified" refers to a peptide, peptide analog, or antibody that is greater than about 90% or greater than about 95% pure. Most preferably it refers to a peptide, peptide analog, or antibody that is greater than 99% pure. Functionally, "substantially purified" means that it is free from contaminants to a degree that that makes it suitable for the purposes provided herein. Other embodiments provide for the prophylactic administration of the peptides to those at risk for *Flavivirus* infection.

Other embodiments of the instant invention provide for methods for identifying the structure of truncated *Flavivirus* fusion proteins which involved in virion:cell fusion by members of the Flaviviridae family and for the structures themselves.

Other embodiments of the invention provide for a peptide having a formula selected from one or more of the following.

A. Various embodiments of the invention provide for hepatitis C virus Fusion Inhibitory Peptides: hepatitis C virus Fusion Inhibitory Protein 1, X-YQVRNSSGLYHVTNDCPNS-SIVYEAADAIL-Z (SEQ ID NO:1); HCV Fusion Inhibitory Protein 2, X-CSALYWVGDLCGSVFLVGQLFTF-SPRRHWTTQDC-Z (SEQ ID NO:2); HCV Fusion Inhibitory Protein 3, X-SPRRHWTTQDCNCSIYPGHITGHR-MAWDMMMNWSPT-Z (SEQ ID NO:3); or HCV Fusion Inhibitory Protein 4, X-MMMNWSPTAALLRIPQAIMD-MIAGAHWGVLAGIKYFSMVGNW-Z (SEQ ID NO:4)

B. Other embodiments of the invention provide for a peptide or peptide homolog wherein. the *Flavivirus* is member or tentative member of the *hepacivirus* genus. A preferred embodiment of this invention is drawn to a peptide or peptide analog wherein the tentative member of the *hepacivirus* genus is hepatitis G virus and peptides are selected from the group consisting of: hepatitis G virus Fusion Inhibitory Peptides: hepatitis G virus Fusion Inhibitory Protein 1, X-RVT-DPDTNTTILTNCCQRNQVIYCSPSTCL-Z (SEQ ID NO:5); hepatitis G virus Fusion Inhibitory Protein 2, X-TCDALDIGELCGACVLVGDWLVRHWLI-HIDLNET-Z (SEQ ID NO:13); hepatitis G virus Fusion Inhibitory Protein 3, X-IHIDLNETGTCYLEVPTGIDPG-FLGFIGWMAGKVEA-Z (SEQ ID NO:21); or hepatitis G virus Fusion Inhibitory Protein 4, X-WMAGKVEAVIFLT-KLASQVPYAIATMFSSVHYLAVGALIYYS-Z (SEQ ID NO:29)

C. Other embodiments of the invention provide for a peptide or peptide homolog from the *flavivirus* genus. In a preferred aspect of this embodiment, the peptide or peptide analog is from dengue virus and the peptides are selected from the group consisting of dengue virus Fusion Inhibitory Peptides: dengue virus Fusion Inhibitory Protein 1, X-RDFVEG-VSGGSWVDIVLEHGSCVTTMAKNKPTLDF-Z (SEQ ID NO:6); dengue virus Fusion Inhibitory Protein 2, X-KRFVCKHSMVDRGWGNGCGLFGKGGIVT-CAMFTC-Z (SEQ ID NO:14); dengue virus Fusion Inhibitory Protein 3, X-MVLLQMEDKAWLVHRQWFLDLPLP-WLPGADTQGSNW-Z (SEQ ID NO:22); or dengue virus Fusion Inhibitory Protein 4, X-MVILGDTAWDFGSLG-GVFTSIGKALHQVFGAIYGAAFSGVSW-Z (SEQ ID NO:30).

D. Other embodiments of the invention provide for peptides or peptide homolog from *flavivirus* genus member, Japanese encephalitis virus. In preferred aspects of these embodiments the peptides and or/peptide analogs are selected from the group consisting of: Japanese encephalitis virus Fusion Inhibitory Peptides: Japanese encephalitis virus Fusion Inhibitory Protein 1, X-RDFIEGASGATWVDLVLEGD-SCLTIMANDKPTLDV-Z (SEQ ID NO:7); Japanese encephalitis virus Fusion Inhibitory Protein 2, X-SSYVCK-QGFTDRGWGNGCGLFGKGSIDTCAKFSC-Z (SEQ ID NO:15); Japanese encephalitis virus Fusion Inhibitory Protein 3, X-FYVMTVGSKSFLVHREWFHDLALP- WTSPSSTAWRNR-Z (SEQ ID NO:23); or Japanese encephalitis virus Fusion Inhibitory Protein 4, X-LAALGD-TAWDFGSIGGVFNSIGKAVHQVFG-GAFRTLFGGMSW-Z (SEQ ID NO:31).

E. Other embodiments of the invention provide for peptides and/or peptide homologs wherein the member of the *flavivirus* genus is yellow fever virus and the peptides are selected from the group consisting of: yellow fever virus Fusion Inhibitory Peptides: yellow fever virus Fusion Inhibitory Protein 1, X-RDFIEGVHGGTWVSATLEQDKCVTVMAP-DKPSLDI-Z (SEQ ID NO:8); yellow fever virus Fusion Inhibitory Protein 2, X-GDNACKRTYSDRGWGNGCGLF-GKGSIVACAKFTC-Z (SEQ ID NO:16); yellow fever virus Fusion Inhibitory Protein 3, X-SYIAEMETESWIV-DRQWAQDLTLPWQSGSGGVWREM-Z (SEQ ID NO:24); or yellow fever virus Fusion Inhibitory Protein 4, X-LAVMGDTAWDFSSAGGFFTS-VGKGIHTVFGSAFQGLFGGLNW-Z (SEQ ID NO:32).

F. Other embodiments of the invention provide for peptides and/or peptide homologs of wherein the member of the *flavivirus* genus is West Nile virus and the peptides are selected from the group consisting of: West Nile virus Fusion Inhibitory Peptides: West Nile virus Fusion Inhibitory Protein 1, X-RDFLEGVSGATWVDLVLEGDSCVTIM-SKDKPTIDV-Z (SEQ ID NO:9); West Nile virus Fusion Inhibitory Protein 2, X-PAFVCRQGVVDRGWGNGCGLF-GKGSIDTCAKFAC-Z (SEQ ID NO:17); West Nile virus Fusion Inhibitory Protein 3, X-YYVMTVGTKT-FLVHREWFMDLNLPWSSAGSTVWRNR-Z (SEQ ID NO:25); or West Nile virus Fusion Inhibitory Protein 4, X-LAALGDTAWDFGSVGGVFTS-VGKAVHQVFGGAFRSLFGGMSW-Z (SEQ ID NO:33).

G. Other embodiments of the instant invention provide for peptides and/or peptide homologs wherein the *Flavivirus* is a member of the *pestivirus* genus. In various aspects of these embodiments he peptides or homologs thereof the member of the *pestivirus* genus is classical swine fever virus and the peptides are selected from the group consisting of: classical swine fever virus Fusion Inhibitory Peptides: classical swine fever virus Fusion Inhibitory Protein 1, X-GQLACKEDYRYAISSTNEIGLLGAG-GLTTTWKEYN-Z (SEQ ID NO:10); classical swine fever virus Fusion Inhibitory Protein 2, X-KGKYNTTLLNG-SAFYLVCPIGWTGVIECTAVSPT-Z (SEQ ID NO:18); or classical swine fever virus Fusion Inhibitory Protein 3, X-TL-RTEVVKTFRRDKPFPHRMDAVTTTVENEDLFY-Z (SEQ ID NO:26); or classical swine fever virus Fusion Inhibitory Protein 4, X-QQYMLKGEYQYWFDLDVTDRHSDY-FAEFVVLVVVALLGGRYI-Z (SEQ ID NO:34).

H. Other embodiments of the instant invention provide for peptides and peptide homologs wherein the member of the *pestivirus* genus is bovine viral diarrhea virus and the peptides are selected from the group consisting of: bovine viral diarrhea virus Fusion Inhibitory Peptides: bovine viral diarrhea virus Fusion Inhibitory Protein 1, X-GHLDCKPEF-SYAIAKDERIGQLGAEGLTTTWKEYS-Z (SEQ ID NO:11); bovine viral diarrhea virus Fusion Inhibitory Protein 2, X-RGKFNTTLLNGPAFQMVCPIGWT-GTVSCTSFNMD-Z (SEQ ID NO:19); or bovine viral diarrhea virus Fusion Inhibitory Protein 3, X-TLATEV-VKIYKRTKRFRSGLVATHTTIYEEDLYH-Z (SEQ ID NO:27); or bovine diarrhea virus Fusion Inhibitory Peptide 4, X-QQYMLKGEYQYWFDLEVTDHHRDY-FAESILVVVVALLGGRYV-Z (SEQ ID NO:35).

I. Other embodiments of the instant invention provide for peptides and peptide homologs wherein the member of the *pestivirus* genus is border disease virus and the peptides are selected from the group consisting of: border disease virus Fusion Inhibitory Peptides: classical swine fever virus Fusion Inhibitory Protein 1, X-GEFACREDHRYALAKTKEIGPL-GAESLTTTWTDYQ-Z (SEQ ID NO:12); border disease virus Fusion Inhibitory Protein 2, X-RGKYNATLLNG-SAFQLVCPYEWTGRVECTTISKS-Z (SEQ ID NO:20); or border disease virus Fusion Inhibitory Protein 3, X-TLAT-TVVRTYRRSKPFPHRQGAITQKNLGEDLH-Z (SEQ ID NO:28); or border disease virus Fusion Inhibitory Peptide 4, X-QQYMLKGQYQYWFDLEVISSTH-QIDLTEFIMLAVVALLGGRYV-Z (SEQ ID NO:36)

In any of the foregoing groups the amino acids are represented by the single letter code. In various aspects of these embodiments "X" comprises an amino group, an acetyl group, a hydrophobic group or a macromolecular carrier group; "Z" comprises a carboxyl group, an amido group a hydrophobic group or a macromolecular carrier group. In other aspects of this embodiment of the invention, X is a hydrophobic group, a carbobenzoxyl group, a dansyl group, t-butyloxycarbonyl group, a lipid conjugate, a polyethylene glycol group, or a carbohydrate. In any aspect of this embodiment Z may be a t-butyloxycarbonyl group, a lipid conjugate, a polyethylene glycol group, or a carbohydrate.

Moreover, aspects of this embodiment also include peptides wherein at least one bond linking adjacent amino acids. residues is a non-peptide bond. In particularly preferred aspects of this embodiment the non-peptide bond is an imido, ester, hydrazine, semicarbazoide or azo bond.

Other aspects of this embodiment provide for peptides wherein at least one amino acid is a D-isomer amino acid.

Additional aspects of this embodiment of the invention provide for peptides wherein compromising at least one amino acid substitution has been made so that a first amino acid residue is substituted for a second, different amino acid residue. These substitutions may be conservative or non-conservative. So long as the peptide is still functional according to the instant invention.

Other aspects of this embodiment of the invention provide for peptides wherein at least one amino acid has been deleted. As noted, supra, the peptides according to this embodiment of the invention must comprise at least 3 contiguous amino acids of one of the SEQ ID NOs indicated above and must be a functional segment.

It is noted that any combination of the modifications listed above is considered as part of the instant invention.

6. EXAMPLE

HEPATITIS C VIRUS E1 IS A TRUNCATED CLASS II FUSION PROTEIN

Proteomics computational tools were used to fit HCV E1 protein to the scaffold of TBEV E, the prototypic class II fusion protein. Because HCV E1 is shorter than TBEV E, we reasoned that the former might contain several "deletions" relative to the latter. The HCV E1 fusion peptide (Flint et al., 1999) was assumed to be located at the end of the molecule furthest from the carboxyl terminal (C-terminal) transmembrane anchor domain, and, like other class II fusion proteins to be comprised mostly of antiparallel β-sheets. This latter assumption was supported by Chou-Fasman (Chou and Fasman, 1974) and Robson-Garnier (Biou et al., 1988) analyses, the most commonly applied secondary structure prediction algorithms.

The fusion peptide of HCV (amino acids [aa] 272 to 281 of the full-length polyprotein) was aligned with the fusion peptide of TBEV E (aa 385-396) (FIG. 1A). Both TBEV E and HCV E1 fusion peptides have cysteine residues at either end and contain a core of mostly aromatic and hydrophobic amino acids (FIG. 1A). Another domain readily identifiable in HCV E1 is the transmembrane domain. Amino acids 361 to 381 of the hydrophobic sequence near the carboxyl terminus of E1 were predicted to form a transmembrane helix by TMpred (transmembrane prediction software, see ch.embnet.org) (TMpred score 1308, >500 is statistically significant).

Figure 1B:
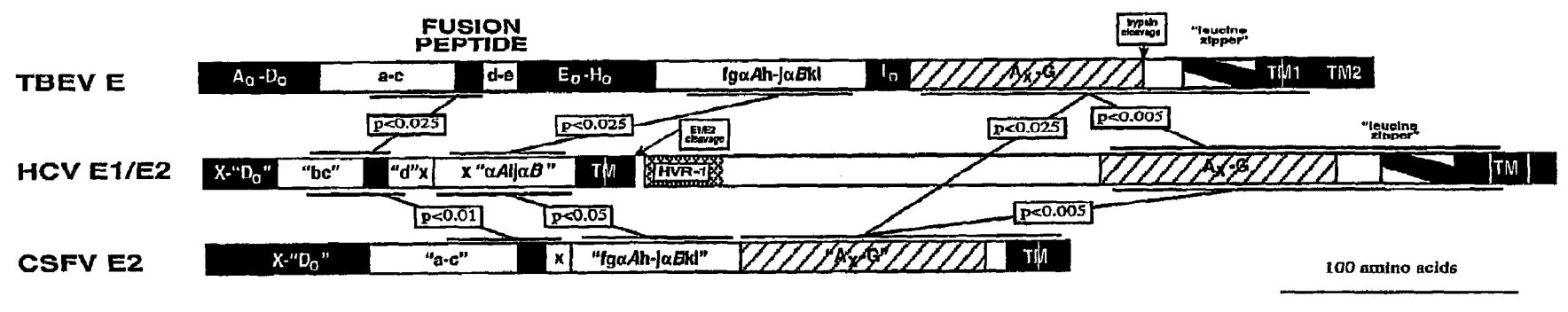

Several regions of predicted β sheets and α helices in HCV E1 showed similarities to sequences known to assume those secondary structures in TBEV E (FIG. 1A). Beginning from the amino terminus, the first similarity of HCV E1 begins in β sheet $D_o$ of TBEV E and extends through the fusion peptide. PRSS3, a sequence alignment algorithm, was used to confirm that there is a significant similarity ($p<0.025$) between amino acids 246-281 of HCV E1 and amino acids 350-396 of TBEV E (FIG. 1B). The fusion peptide is flanked by β sheets in class II fusion proteins and predicted β sheets with similarities to the b and c β sheets of TBEV E are indeed predicted to be present on either side of the putative HCV E1 fusion peptide by Chou-Fasman and Robson-Garnier analysis. HCV E1 also has an extended region of similarity with the amino acid sequence between the two longest helices in TBEV E, αA and αB. There is a statistically significant ($P<0.025$) alignment of amino acids 316-356 of HCV E1 with amino acids 496-544 of TBEV E (FIG. 1B).

To determine the plausibility of these alignments, a three-dimensional model of HCV E1 was scaffolded on domain II of TBEV E (FIG. 2A). Similar sequences/structures were drawn in similar locations. Reorienting the "b" sheet in E1 is the only change relative to E required to bring the eight cysteine residues into close proximity. The four dicysteines of HCV E1 potentially form a "zipper" down the center of the molecule like the three dicysteines in domain II of TBEV E (FIG. 2B). This model locates the five HCV E1 glycosylation sites so they are surface accessible. Additionally, most of the hydrophobic residues are present in a region on one side of E1 between the fusion peptide and the transmembrane anchor (see below, FIG. 5).

Each of the HCV E1 structures drawn in FIG. 2B conforms to both Chou-Fasman and Robson-Garnier predictions, with the exception of the region from "i" to "αB". The structures designated "i" and "j" were predicted to be β sheets by Chou-Fasman analysis, but α helical by Robson-Garnier analysis. The structure designated "αB" was predicted to be a β sheet by Chou-Fasman analysis, but α helical by Robson-Garnier analysis. HCV E1 appears to be missing, relative to TBEV E, much of the portion of the molecule prior to the transmembrane helix (pre-anchor). This region of TBEV E follows the trypsin cleavage site at amino acid 395 used to generate that portion of the ectodomain of E examined by X-ray crystallography, and therefore, the TBEV E pre-anchor (stem) structure is uncertain. The pre-anchor of TBEV E has been predicted to form an amphipathic α helix (Allison et al., 1999). A sequence (aa 693-721) of the pre-anchor domain in TBEV E has the characteristics of a leucine zipper, i.e. leucine or another hydrophobic amino acid in the first and fourth (a and d) positions of a seven amino acid periodicity (FIG. 1A). The pre-anchor sequence of HCV E1 was also predicted to be an α helix with characteristics of a "leucine zipper" (Charloteaux et al., 2002). Because of the significant amino acid sequence similarity with TBEV E, the HCV E1 secondary structures between "αA" and "αB" were depicted as in TBEV E. There are several possible alternatives to the 3D model of HCV E1 drawn in FIG. 2B, and it is possible that the secondary structures change on interaction with membranes.

In contrast to HCV E1, our analyses did not reveal any sequences of HCV E2 with significant similarity to any sequence in domains I or II of TBEV E or any other *flavivirus* E protein (representatives of each of the four major serogroups were examined). Most of the N-terminal half of HCV E2, which include hypervariable region 1 (HVR 1), is without any sequence similarity to TBEV E. However, we detected a significant alignment ($p<0.025$) of the C-terminal half of HCV E2 (aa 549-726) with the region of TBEV E (aa 590-763) from domain III through the first of two predicted transmembrane spanning domains of TBEV E (FIG. 1, TBEV E TM1, amino acids 448-469, TMpred: 1496; TM2, amino acids 474-496, TMpred: 1962). As discussed above, the pre-anchor region of TBEV E has a sequence (aa 693-721) with features of a "leucine zipper; a similar motif (aa 675-703) is found in the HCV E2 pre-anchor (FIG. 1). In addition, the carboxyl (C) terminus of HCV E2, like that of TBEV E, contains a stretch of hydrophobic amino acids that potentially could span the membrane twice. The transmembrane anchor(s) of HCV E2 (TMpred score: 1364) is interrupted by charged amino acids like TM1 of TBEV E. Thus, by sequence alignments and structural predictions there are demonstrable similarities between the C-terminal portions of HCV E2 and TBEV E.

Significant alignments of E1 of hepatitis GB virus (GBV-B) with HCV E1, indicate that this unclassified member of the Flaviviridae family also encodes a truncated class II fusion protein.

6.1. Materials and Methods

Prototype strains of representatives of the Flaviviridae were used for sequence and structural comparisons. The strains examined include TBEV strain Neudoerfl (accession number: P14336); and the human prototype strain H (subtype 1a) of hepatitis C virus (P27958), Some comparisons used representatives of the major serogroups of *flaviviruses*, including Japanese encephalitis virus, strain JaOARS982 (P32886), yellow fever virus, strain 17D-204 (P19901), dengue virus type 2, strain PR-159/S1 (P12823), and West Nile virus, strain NY 2000-crow3356 (AF404756). We also compared HCV sequences to those of GB virus-B virus (AAC54059), an unassigned member of the Flaviviridae.

MACMOLLY®, protein analysis software (Soft Gene GmbH, Berlin), was used to locate areas of limited sequence similarity and to perform Chou-Fasman and Robson-Garnier analyses. PRSS3, a program derived from rdf2 (Pearson and Lipman, 1988), which uses the Smith-Waterman sequence alignment algorithm (Smith and Waterman, 1981), was used to determine the significance of protein alignments. PRSS3 is part of the FASTA package of sequence analysis programs available by anonymous ftp from ftp.virginia.edu. Default settings for PRSS3 were used, including the blosum50 scoring matrix, gap opening penalty of 12, and gap extension penalty of 2. The alignments presented are those that produced the highest alignment scores, rather than the longest sequences that produced significant scores. Chou-Fasman and Robson-Garnier algorithms predict protein structures in an aqueous environment, but they cannot predict protein structures in a lipid bilayer. Domains with significant propensity to form transmembrane helices were identified with TMpred (ExPASy, Swiss Institute of Bioinformatics). TMpred is based on a statistical analysis of TMbase, a database of naturally occurring transmembrane glycoproteins (Hofmann and Stoffel, 1993). RasMac, developed by Roger Sayle, was used to render 3D models of TBEV E.

6.2. Results and Discussion

The results indicate that the ectodomain of *hepaciviruses* is a truncated version of the class II fusion protein structure. The ectodomain of HCV E1 is roughly equivalent to the part of TBEV E from the "hinge" region to the fusion peptide (FIG. 2). Our conclusions contrast with those of Yagnik et al. (2000), who predicted that HCV E2 fits the scaffold of a complete class H fusion protein. These models were not previously described. Yagnik et al. (2000), taught that HCV E2 fits the scaffold of a complete class II fusion protein. Lescar and co-workers (2001) stated that their structural determinations of SFV E1, which established the existence of a second class of fusion proteins, "indeed support the proposed model of the hepatitis C virus envelope protein E2 which was based on the 3D structure of the *flavivirus* envelope protein E." In contrast our model indicated that HCV E1 is class II although not similar to that previously described. Although there are sequence and structural similarities between HCV E2 and TBEV E, these similarities are limited to the C-terminal portions of these proteins, and are different than those proposed previously (Yagnik et al., 2000).

7. EXAMPLE

*PESTIVIRUS* E2 IS A TRUNCATED CLASS II FUSION PROTEIN

To provide additional evidence for the HCV E1 class II fusion protein model, we determined whether the fusion proteins of the third *Flaviviridae* genus, pestiviruses, might share structural/sequential similarities with fusion proteins of members of the *flavivirus* and *hepacivirus* genera. *Pestiviruses* encode three envelope glycoproteins, Erns, E1 and E2. Erns, a secreted protein with RNAse activity, does not have a hydrophobic transmembrane anchor domain. Erns does possess a C-terminal charged amphipathic segment that can mediate translocation of Erns across bilayer membranes (Langedijk, 2002). *Pestivirus* E1 and E2 both have C-terminal hydrophobic domains that could function as transmembrane anchors. Therefore, we postulated that either *pestivirus* E1 or E2 must be the *pestivirus* fusion protein.

A putative fusion peptide (aa 818-828) is present in CSFV E2, containing a consensus sequence with aromatic and hydrophobic amino acids located between two cysteine residues (FIG. 1). The cysteine residues as well as the sequences in between are highly conserved among *pestiviruses*, as is true of fusion peptides from other enveloped RNA viruses of class I and II (not shown). Although statistically significant alignments were not detected between the N-terminus of CSFV E2 and TBEV E (or between other *flaviviruses*), a significant alignment ($p<0.01$) was detected between CSFV E2 (aa 792-835) and HCV E1 (aa 253-294) in this region (FIG. 1B). Furthermore, sequences flanking the putative fusion peptide were predicted to form β sheets by both Chou-Fasman and Robson-Garnier analyses (supplemental data). A significant alignment ($p<0.05$) between CSFV E2 (aa 841-913) and HCV E1 (aa 301-383) was also determined. By extension, the central portion of CSFV E2 is predicted to structurally resemble domain II of TBEV E. A significant alignment ($p<0.005$) was detected between amino acids 914-1018 of CSFV E2 and a sequence in domain III of TBEV E (aa 587-685) (FIG. 1B). There was also a significant similarity ($p<0.005$) of this region of CSFV E2 (aa 914-1123) with a sequence (aa 549-743) in the region of HCV E2 that aligns with TBEV domain III. In addition, TMpred confirmed that the hydrophobic C-terminal domain of CSFV E2 has a high propensity to span the lipid bilayer (score: 1137). Like the transmembrane domains of HCV E1/E2 and TBEV TM1, the putative transmembrane anchor of CSFV E2 has a central positive charge.

On the basis of the regions of significant sequence similarities between CSFV E2, HCV E1/E2 and TBEV E, coupled with the internal location of a possible fusion peptide, we conclude that relative to TBEV E, CSFV E2 is lacking a portion of domain I including segments corresponding to β sheets $E_o$ through $I_o$. CSFV E2 also appears to contain a somewhat shorter segment relative to TBEV E in the pre-anchor domain, i.e. the sequence between the alignment with TBEV E domain III and the transmembrane domain (FIG. 1B). No leucine zipper is evident in the pre-anchor of CSFV E2. A three dimensional model of CSFV E2 (FIG. 2C) confirms that the alignment in FIG. 1 is plausible. Each of the cysteine residues is in proximity to other cysteine residues and potentially form dicysteine bridges. Like HCV E1, CSFV E2 conforms to the structure of a truncated class II fusion protein, albeit with fewer truncations relative to *flavivirus* E than HCV E1. Because E2 is conserved among the *pestivirus* genus, the similarities of CSFV E2 with TBEV E extend to other *pestiviruses*.

None of the E1 envelope glycoproteins of any *pestivirus* bear any significant sequence similarities to any sequenced *flavivirus* E protein. Immature *flavivirus* virions contain a precursor, prM, to the small membrane protein M. prM is cleaved in the endoplasmic reticulum by furin or by a furin-like protease during virus release to produce the mature M protein localized on the surface of *flavivirus* virions (Stadler et al., 1997). A sequence (amino acids 173-256) of CSFV E1 has similarity ($p=0.030$) to amino acids 583-654 of TBEV prM (FIG. 3A). CSFV E1 does not contain the sequence RXR/KR (SEQ ID NO:37), the furin consensus cleavage site. CSFV E1 also does not contain an identifiable fusion peptide, although TMpred predicts a significant transmembrane spanning domain in the first third of CSFV E1. Like the transmembrane domains of TBEV E, HCV E1 and E2 and CSFV E2, and TBEV prM (TMpred score=1828), the C-terminus of CSFV E1 is predicted to form a membrane spanning domain (TMpred score=1884) with a central positive charge.

7.1. Materials And Methods

The Alfort 187 strain of classical swine fever virus, aka hog cholera virus (CAA61161) was used as the prototype of the *pestivirus* genus of the family Flaviviridae. Type species of other *pestiviruses*, including bovine viral diarrhea virus (BVDV) genotype 1, aka *pestivirus* type 1, strain NADL (CAB91847) and border disease virus strain BD31 (AAB37578), were used in other comparisons. Proteomics computational methods were as described in 6.1.

7.2. Results And Discussion

*Pestivirus* E2 proteins are truncated class II fusion proteins, although with fewer truncations relative to *flavivirus* E than *hepacivirus* E1.

8. EXAMPLE

GENE ORDER OF FLAVIVIRIDAE GENOMES

Genes that encode proteins with similar functions may be present in similar locations in genomes of different members of the Flaviviridae family. The positive-polarity single-stranded RNA genomes of all members of the Flaviviridae are translated into a single large polyprotein that is subsequently cleaved by viral and cellular proteases into functional proteins. The order (from N to C terminus) of proteins in the polyproteins of TBEV and other members of the *flavivirus* genus is C-prM-E-nonstructurals (C: capsid), and the order of proteins in the polyproteins of *hepaciviruses* is C-E1-E2-p7-nonstructurals (FIG. 4). The 5' portion of the *flavivirus* E gene encodes the fusion peptide in domain II of the E protein, whereas the receptor binding domain of E is probably located in domain III encoded by the 3' portion of the E gene (Crill and Roehrig, 2001; Mandl et al., 2000). Fusion and receptor functions may reside in two different HCV proteins, E1 and E2 respectively, occurring in the same order as the domains of *flavivirus* E that carry out these functions (FIG. 4). *Hepacivirus* E1 and E2 may have arisen by insertion of a transmembrane anchor and variable domains, including hypervariable region 1 (HVR-1, FIG. 1), into the ancestral E gene. Alternatively, HCV E1 could have evolved into a separate fusion protein from an ancestral prM, with concurrent lost of the fusion peptide and fusion functions in E2. The sequence similarities between TBEV E and HCV E1 and E2, however, do not favor this latter possibility.

The order of proteins in *pestivirus* polyproteins is Npro-C-Erns-E1-E2-p7-nonstructurals. *Pestiviruses* encode two proteins, Npro and $E^{rns}$, with no obvious homologs among members of the other two Flaviviridae genera. *Pestivirus* E1 and E2 are similar in sequence to *flavivirus* M and E, respectively. Like TBEV E, *pestivirus* E2 may serve both as fusion protein and receptor binding protein. These functions are carried out by TBEV E domains II and III that appear to be represented by similar structures in *pestivirus* E2 (FIG. 4). TBEV PrM/M functions to protect internal cellular membranes from fusion mediated by E2, and it is possible that *pestivirus* E1 serves the same function for E2, the fusion/receptor protein. Excepting Npro and $E^{rns}$, the order of structural proteins with sequence and other similarities is analogous in *pestiviruses* and *flavivirus* polyproteins.

TBEV E has two hydrophobic C-terminal transmembrane domains, TM1 and TM2 (FIG. 1). *Hepaciviruses* and *pestiviruses* encode a small hydrophobic peptide, "p7", which could associate with cellular or viral membranes. The cleavage that produces p7 is inefficient and delayed, and therefore much of HCV E2 and *pestivirus* E2 are present in the cell as uncleaved E2-p7 precursors (Harada, Tautz, and Thiel, 2000). The p7 gene is located in a similar genomic location and could have evolved from the sequence encoding the second transmembrane domain, TM2, of *flavivirus* E (FIG. 4). The consensus Flaviviridae genome can therefore be represented as X1-C-X2-M-fusion-binding-TM1-TM2-nonstructurals-3', where X 1 and X2 represents inserted sequences in *pestiviruses*, $N^{pro}$ and $E^{rms}$, respectively, M represents *flavivirus* prM/M-*pestivirus* E1 and TM2 is the second transmembrane domain of *flaviviruses* and p7 of *hepaciviruses* and *pestiviruses*. These similarities in gene order and functions support the hypothesis that E1 is the fusion protein of HCV.

8.1. Materials And Methods

Prototype strains of representatives of the Flaviviridae as described in 6.1 and 7.1 were used for sequence comparisons.

8.2. Results And Discussion

*Hepaciviruses*, like *alphaviruses*, appear to use one envelope protein for attachment (E2) and another for fusion (E1). In contrast, E glycoproteins of TBEV, dengue virus, and other members of the *flavivirus* genus mediate both receptor binding and membrane fusion functions. E2 functions as one of the *pestivirus* receptor-binding protein (Hulst and Moormann, 1997), and if the current analysis is correct also carries out the virion:cell fusion function. In addition to E, *flaviviruses* encode a membrane protein prM whose functions may include shielding of cellular membranes from the fusion peptide of E (Kuhn et al., 2002). Functions of the *flavivirus* small membrane protein may be vested in E1 of *pestiviruses*, which has significant sequence similarity with *flavivirus* prM. Mature flavivirus virions contain prM that has been cleaved to M. Unlike M, *pestivirus* E1 does not associate with the virion envelope as a precursor protein and lacks a furin cleavage site.

The *Flavivirus* fusion protein structures and functional domains described here are supported by the observations that envelope glycoproteins with significant sequence similarities, HCV E1/2, TBEV E and *pestivirus* E2 and TBEV prM and *pestivirus* E1 are in analogous locations in the polyproteins encoded by the three genera of the *Flaviviridae*. These results suggest that members of the Flavivirus family may have a common ancestor. Divergence of the genes for the fusion proteins within the three genera of this family may have occurred either through acquisition of sequences and/or lose of sequences in a cassette manner constrained by the domain organization of class II fusion proteins.

9. EXAMPLE

MEMBRANE INTERFACIAL DOMAINS IN A CLASS I FUSION PROTEIN AND HCV E1

Although the overall structures of class I and II fusion proteins are distinct, they may share structural/functional characteristics in the parts of the molecules that interact with and disrupt bilayer membranes. It is well established that class I fusion proteins have a fusion peptide at the amino terminus of the molecule that is critical for fusion (Gallaher, 1987; Gallaher, 1996; Gallaher et al., 1989; Gallaher, DiSimone, and Buchmeier, 2001). Class II fusion proteins have an internal fusion peptide that are located after secondary structural folding at distal locations from the transmembrane anchor (Kuhn et al., 2002; Lescar et al., 2001; Rey et al., 1995). To provide further support for the proposed models of HCV E1 and *pestivirus* E2, we used another proteomics computational tool to compare other potential membrane interactive domains in the proteins with the HIV-1 transmembrane glycoprotein (M), a class I fusion protein. Besides fusion peptides, another motif in class I fusion proteins that can be important in virus:cell fusion is an aromatic amino acid rich motif proximal to the anchor (FIG. 5A, amino acids 667-683) (Suarez et al., 2000). The pre-anchor domains of class I fusion proteins are not highly hydrophobic according to the Kyte-Doolittle hydropathy prediction algorithm, however, these domains have a tendency to partition into bilayer membranes, as revealed by analyses using the Wimley-White interfacial hydrophobicity scale (Suarez et al., 2000; Wimley and White, 1996). HCV E1 contains three domains that produce significant Wimley-White partition scores using Membrane Protein explorer (Jaysinghe, Hristova, and White, 2000). One of these is the transmembrane anchor (aa 361-372). The other two sequences with significant Wimley-White partition scores are located immediately following the fusion peptide (aa 284-300) and at a location (aa 321-340) that the model in FIG. 2B predicts to be near the bilayer membrane (FIG. 5B).

9.1. Materials And Methods

Sequences with a propensity to partition into the lipid bilayer were identified with Membrane Protein eXplorer from the Stephen White laboratory (Jaysinghe, Hristova, and White, 2000) using default settings.

9.2. Results And Discussion

These two HCV E1 domains, in conjunction with the fusion peptide and the transmembrane anchor, potentially form a continuous track of membrane interactive regions that could channel the movement of lipids during virion:cell fusion. These Wimley-White partition analyses thus provide additional support for the proposal that E1 is the fusion protein of HCV.

10. EXAMPLE

IDENTIFICATION OF PEPTIDES THAT INHIBIT FUSION/INFECTIVITY MEDIATED BY HCV ENVELOPE PROTEINS

The membrane fusogenic envelope glycoproteins of *Flaviviruses* share several common structural features, including "fusion peptides" and globular domain structures consisting mostly of antiparallel β sheets. Furthermore, the E1 protein of HCV and the E proteins of DEN, WNV and YFV each have several motifs with a high propensity to interact with bilayer membranes as revealed by algorithms employing the Wimley-White interfacial hydrophobicity scale. These structural features and membrane interfacial motifs are presumably important in *Flavivirus* fusion, entry and infection and may represent targets to develop peptide drugs against *Flavivirus* infection.

10.1. Materials And Methods

To overcome the lack of a conventional cell culture system for the propagation of HCV, infectious pseudotype viruses expressing HCV envelope glycoproteins have been generated (Hsu et al., 2003). Pseudotypes with HIV core proteins and HCV envelope proteins were generated by cotransfection of 293-T cells with equal amounts of plasmids expressing HCV E1 and E2 of strain H77 and the HIV envelope-defective proviral genome, pNL4.3.Luc.R⁻E⁻ (Pohlmann et al., 2003). Peptides from an 18mer peptide set, overlapping by 7-10 amino acids and representing the entire amino acid sequence of E1 of HCV strain H77, were solubilized in 20% DMSO, diluted (final DMSO concentration <2%). Peptides were incubated on ice for 30 minutes with p24 antigen-normalized HCV pseudotype viral supernatants. The average concentration of peptides was ~25 µM, however, actual concentrations of some peptides in solution were 10 µM or less due to low solubility in DMSO (marked by asterisk in Table 5). Supernatants were also treated with DMSO vehicle alone or with a Mab (monoclonal antibody) to HCV E2 known to neutralize pseudotype infectivity. HCV peptides, vehicle, and anti-E2 MAb were also incubated with pseudotypes expressing murine leukemia virus (MLV) envelope proteins and HIV capsid proteins to control for cytotoxicity. Peptide treated and control HCV and MLV pseudotypes were added to cells, which were incubated at 37° C. for 72 h. Cell lysates were then tested for luciferase activity as described (Hsu et al., 2003).

10.2 Results and Discussion

Four HCV E1 peptides demonstrated greater than 70% inhibition of HCV pseudotype infectivity, with one (peptide 54) reducing HCV pseudotype infectivity by >99.9% (Table 5, FIG. 5B). Two of the peptides (66 and 70) correspond to sequences with a high propensity to interact with the surface of bilayer membranes, as determined by application of the Wimley-White interfacial hydrophobicity scale. Peptide 66 also inhibited infection by the HIV(MLV) pseudotype by greater that 50% suggesting either that this peptide is a general inhibitor of viral fusion or that it is cytotoxic. The other two inhibitory peptides (54 and 74) represent sequences of HCV E1 predicted to "fold" over and interact with the portion of E1 displaying high Wimley-White interfacial hydrophobicity scores (FIG. 5B). The postulated folding over of these domains was marked by arrows in the original published figure (FIG. 5 of Garry and Dash, 2003,). These results demonstrate the potential of peptides as antiHCV drugs, and indicate that similar strategies can identify peptides that inhibit fusion and infectivity of other *Flaviviruses*.

TABLE 5

Identification of lead peptides that inhibit infectivity mediated by HCV envelope proteins.

| Peptide number | ‡H77-E1E2† | Percent inhibition | §MLV† | Percent inhibition |
|---|---|---|---|---|
| 52 | 133,259 | −17.16 | 533,179 | −21.4 |
| 53 | 113,469 | 0.23 | 443,528 | −9.95 |
| 54 | 74 | 99.93 | 280,113 | 36.22 |
| 55 | 112,470 | 1.12 | 447,957 | −2.00 |
| 56 | 65,612 | 42.32 | 433,459 | 1.30 |
| 57 | 169,860 | −49.35 | 331,852 | 24.44 |
| 58 | 118,767 | −4.42 | 329,895 | 24.98 |
| 59 | 91,794 | 19.29 | 446,063 | −1.57 |
| 60 | 98,766 | 13.16 | 340,384 | 22.49 |
| 61 | 148,796 | −30.83 | 423,925 | 3.47 |
| 62 | 115,966 | −1.96 | 415,014 | 5.50 |
| 63 | 57,915 | 49.08 | 438,440 | 0.16 |
| 64 | 113,108 | 0.55 | 316,948 | 27.83 |
| 65* | 87,726 | 22.87 | 491,789 | −11.98 |
| 66 | 23,387 | 79.46 | 189,683 | 56.81 |
| 67 | 64,601 | 43.20 | 357,577 | 28.58 |
| 68 | 79,297 | 31.28 | 498,991 | −13.62 |
| 69* | 196,922 | −73.14 | 354,027 | 19.39 |
| 70 | 15,717 | 86.19 | 553,120 | −25.95 |
| 71 | 83,489 | 26.60 | 533,765 | −21.54 |
| 72 | 75,763 | 33.39 | 392,680 | 10.58 |
| 73 | 100,666 | 11.49 | 433,001 | 1.40 |
| 74 | 32,888 | 71.09 | 467,876 | −6.54 |
| 75 | 113,359 | 0.32 | 420,026 | 4.36 |
| 76 | 96,283 | 15.34 | 473,757 | −7.88 |
| 77 | 56,425 | 50.39 | 321,076 | 26.89 |
| 78* | 137,700 | −21.07 | 402,953 | 8.24 |
| 79 | 101,702 | 10.58 | 740,034 | −68.51 |
| Vehicle | 113,733 | — | 439,158 | — |
| anti-E2 | 73 | 99.93 | 349,113 | 21.50 |

‡H77-E1E2 is the pseudotype expressing envelope glycoproteins E1 and E2 of the H77 strain of HCV.
§MLV is a similar pseudotype expressing the envelope glycoprotein of murine leukemia virus and serves as a peptide control.
†The numbers represent the number of luciferase units (lumens) produced after infection by either the HCV or the MLV pseudotype in the presence of the peptide at a concentration of ~25 µM.

TABLE 6

Sequence and Location of peptides shown in Table 5.

| Peptide Number | Peptide Location | Amino acid sequence | FIP overlap |
|---|---|---|---|
| 52 | 183-200 | SCLTVPASAYQVRNSSGL (SEQ ID NO:38) | |
| 53 | 190-207 | SAYQVRNSSGLYHVTNDC (SEQ ID NO:39) | HCV E1 FIP1 |

TABLE 6-continued

Sequence and Location of peptides shown in Table 5.

| Peptide Number | Peptide Location | Amino acid sequence | FIP overlap |
|---|---|---|---|
| 54 | 197-214 | SSGLYHVTNDCPNSSIVY (SEQ ID NO:40) | HCV E1 FIP1 |
| 55 | 204-221 | TNDCPNSSVVYEAADAIL (SEQ ID NO:41) | HCV E1 FIP1 |
| 56 | 211-228 | SIVYEAADAILHTPGCVP (SEQ ID NO:42) | |
| 57 | 218-235 | DAILHTPGCVPCVREGNA (SEQ ID NO:43) | |
| 58 | 225-242 | GCVPCVREGNASRCWVAV (SEQ ID NO:44) | |
| 59 | 232-249 | WVAVTPTVATRDGKLPTT (SEQ ID NO:45) | |
| 60 | 239-256 | WVAVTPTVATRDGKLPTT (SEQ ID NO:46) | |
| 61 | 246-263 | VATRDGKLPTTQLRRHID (SEQ ID NO:47) | |
| 62 | 253-270 | LPTTQLRRHIDLLVGSAT (SEQ ID NO:48) | |
| 63 | 260-277 | RHIDLLVGSATLCSALYV (SEQ ID NO:49) | |
| 64 | 267-284 | GSATLCSALYVGDLCGSV (SEQ ID NO:50) | HCV E1 FIP2 |
| 65 | 274-291 | ALYVGDLCGSVFLVGQLF (SEQ ID NO:51) | HCV E1 FIP2 |
| 66 | 281-298 | CGSVFLVGQLFTFSPRHH (SEQ ID NO:52) | HCV E1 FIP2/3 |
| 67 | 288-305 | GQLFTFSPRHHWTTQDCN (SEQ ID NO:53) | HCV E1 FIP3 |
| 68 | 295-312 | PRHHWTTQDCNCSIYPGH (SEQ ID NO:54) | HCV E1 FIP3 |
| 69 | 302-319 | QDCNCSIYPGHITGHRMA (SEQ ID NO:55) | HCV E1 FIP3 |
| 70 | 309-326 | YPGHITGHRMANMMMNW (SEQ ID NO:56) | HCV E1 FIP3/4 |
| 71 | 316-333 | HRMANMMMNWSPTAALV (SEQ ID NO:57) | HCV E1 FIP3/4 |
| 72 | 323-340 | MMNWSPTAALVVAQLLRI (SEQ ID NO:58) | HCV E1 FIP4 |
| 73 | 330-347 | AALVVAQLLRIPQAIMDM (SEQ ID NO:59) | HCV E1 FIP4 |
| 74 | 337-354 | LLRIPQAIMDMIAGAHWG (SEQ ID NO:60) | HCV E1 FIP4 |
| 75 | 344-361 | IMDMIAGAHWGVLAGIKY (SEQ ID NO:61) | HCV E1 FIP4 |
| 76 | 351-368 | AHWGVLAGIKYFSMVGNW (SEQ ID NO:62) | HCV E1 FIP4 |
| 77 | 359-375 | GIKYFSMVGNWAKVLVVL (SEQ ID NO:63) | |
| 78 | 365-382 | VGNWAKVLVVLLLFAGVD (SEQ ID NO:64) | |
| 79 | 372-389 | LVVLLLFAGVDAETHVTG (SEQ ID NO:65) | |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of each of which is incorporated by reference in its entirety. Citation or identification of any reference in any section of this application shall not be construed as an admission that such reference is available as prior art to the present invention.

REFERENCES

Each of the following is herein incorporated by reference in its entirety.

CHAN, D. C., FASS, D., BERGER, J. M., and KIM, P. S. (1997). Core structure of gp41 from the HIV envelope glycoprotein. *Cell* 89, 263-73.

FLINT, M., THOMAS, J. M., MAIDENS, C. M., SHOTTON, C., LEVY, S., BARCLAY, W. S., and McKEATING, J. A. (1999). Functional analysis of cell surface-expressed hepatitis C virus E2 glycoprotein. *J Virol* 73, 6782-90.

GALLAHER, W. R. (1987). Detection of a fusion peptide sequence in the transmembrane protein of human immunodeficiency virus. *Cell* 50, 327-8.

GALLAHER, W. R. (1996). Similar structural models of the transmembrane glycoproteins of Ebola and avian sarcoma viruses. *Cell* 85, 1-2.

GALLAHER, W. R., BALL, J. M., GARRY, R. F., GRIFFIN, M. C., and MONTELARO, R. C. (1989). A general model for the transmembrane proteins of HIV and other retroviruses. *AIDS Res Hum Retro* 5, 431-40.

GALLAHER, W. R., DISIMONE, C., and BUCHMEIER, M. J. (2001). The viral transmembrane superfamily: possible divergence of *Arenavirus* and *Filovirus* glycoproteins from a common RNA virus ancestor. *BMC Microbiol* 1, 1.

GARRY, R. F. and DASH S. (2003). Proteomics computational analysis suggest that hepatitis C virus E1 and *pestivirus* E2 envelope glycoproteins are truncated class II fusion proteins. *Virology* 307, 255-65.

HOFFMAN-LA ROCHE, and TRIMERIS. (2002). Roche and Trimeris announce 24-week results from second pivotal study of HV fusion inhibitor T-20. trimeris.com/news/pr/2002/020516.html.

HSU, M., ZHANG, J., FLINT, M., LOGVINOFF, C., CHENG-MAYER, C., RICE, C. M., AND MCKEATING, J. A. (2003). Hepatitis C virus glycoproteins mediate pH-dependent cell entry of pseudotyped retroviral particles. *Proc Natl Acad Sci USA* 100, 7271-6.

JAYSINGHE, S., HRISTOVA, K., and WHITE, S. H. (2000). Membrane Protein Explorer. http://blanco.biomiol.usi.edu/mpex.

KUHN, R. J., ZHANG, W., ROSSMANN, M. G., PLETNEV, S. V., CORVER, J., LENCHES, E., JONES, C. T., MUKHOPADHYAY, S., CHIPMAN, P. R., STRAUSS, E. G., BAKER, T. S., and STRAUSS, J. H. (2002). Structure of dengue virus: implications for *flavivirus* organization, maturation, and fusion. *Cell* 108, 717-25.

LESCAR, J., ROUSSEL, A., WIEN, M. W., NAVAZA, J., FULLER, S. D., WENGLER, G., and REY, F. A. (2001). The fusion glycoprotein shell of Semliki Forest virus: an icosahedral assembly primed for fusogenic activation at endosomal pH. *Cell* 105, 137-48.

MALASHKEVICH, V. N., SCHNEIDER, B. J., MCNALLY, M. L., MILHOLLEN, M. A., PANG, J. X., and KIM, P. S. (1999). Core structure of the envelope glycoprotein GP2 from Ebola virus at 1.9-A resolution. *Proc Natl Acad Sci USA* 96, 2662-7.

QURESHI, N., COY, D., GARRY, R., and HENDERSON L A (1990). Characterization of a putative cellular receptor for HIV-1 transmembrane glycoprotein using synthetic peptides. *AIDS* 4, 553-558.

REY, F. A., HEINZ, F. X., MANDL, C., KUNZ, C., and HARRISON, S. C. (1995). The envelope glycoprotein from tick-borne encephalitis virus at 2 A resolution. *Nature* 375, 291-8.

SUAREZ, T., GALLAHER, W. R., AGIRRE, A., GONI, F. M., and NIEVA, J. L. (2000). Membrane interface-interacting sequences within the ectodomain of the human immunodeficiency virus type 1 envelope glycoprotein: putative role during viral fusion. *J Virol* 74, 8038-47.

WEISSENHORN, W., CARFI, A., LEE, K. H., SKEHEL, J. J., and WILEY, D. C. (1998). Crystal structure of the Ebola virus membrane fusion subunit, GP2, from the envelope glycoprotein ectodomain. *Mol Cell* 2, 605-16.

WEISSENHORN, W., WHARTON, S. A., CALDER, L. J., EARL, P. L., MOSS, B., ALIPRANDIS, E., SKEHEL, J. J., and WILEY, D. C. (1996). The ectodomain of HIV-1 env subunit gp41 forms a soluble, alpha-helical, rod-like oligomer in the absence of gp120 and the N-terminal fusion peptide. *EMBO J* 15, 1507-14.

WILD, C., GREENWELL, T., and MATTHEWS, T. (1993). A synthetic peptide from HIV-1 gp41 is a potent inhibitor of virus-mediated cell-cell fusion. *AIDS Res Hum Retro* 9, 1051-3.

WILD, C. T., SHUGARS, D. C., GREENWELL, T. K., MCDANAL, C. B., and MATTHEWS, T. J. (1994). Peptides corresponding to a predictive alpha-helical domain of human immunodeficiency virus type 1 gp41 are potent inhibitors of virus infection. *Proc Natl Acad Sci USA* 91, 9770-4.

WILSON, I. A., SKEHEL, J. J., and WILEY, D. C. (1981). Structure of the haemagglutinin membrane glycoprotein of influenza virus at 3 A resolution. *Nature* 289, 366-73.

YAGNIK, A. T., LAHM, A., MEOLA, A., ROCCASECCA, R. M., ERCOLE, B. B., NICOSIA, A., and TRAMONTANO, A. (2000). A model for the hepatitis C virus envelope glycoprotein E2. *Proteins* 40, 355-66

What is claimed is:

1. A pharmaceutical composition comprising one or more isolated peptides selected from the following:
   a) a peptide consisting of SEQ ID NO:30, wherein the peptide's N-terminal chemical moiety is an amino group and the peptide's C-terminal chemical moiety is a carboxyl group; or
   b) a peptide consisting of SEQ ID NO:30, wherein the peptide's N-terminal chemical moiety is selected from the group consisting of an acetyl group, a hydrophobic group, a carbobenzoxyl group, a dansyl group, a t-butyloxycarbonyl group, and a macromolecular group; or wherein the peptide's C-terminal chemical moiety is selected from the group consisting of an amido group, a hydrophobic group, a t-butyloxycarbonyl group and a macromolecular group.

2. The composition of claim 1 wherein the selected peptide consists of SEQ ID NO:30, wherein the peptide's N-terminal moiety is an amino group and the peptide's C-terminal moiety is a carboxyl group.

3. The composition of claim 1 wherein the selected peptide consists of SEQ ID NO:30, wherein the peptide's N-terminal chemical moiety is an acetyl group, a hydrophobic group, a carbobenzoxyl group, a dansyl group, a t-butyloxycarbonyl group, or a macromolecular group; or wherein the peptide's C-terminal chemical moiety is an amido group, a hydrophobic group, a t-butyloxycarbonyl group or a macromolecular group.

4. The composition of claim 3 wherein the N-terminal chemical moiety is a macromolecular group selected from a lipid conjugate, polyethylene glycol, or a carbohydrate; or wherein the C-terminal chemical moiety is a macromolecular group selected from a lipid conjugate, polyethylene glycol, or a carbohydrate.

* * * * *

SEQUENCE LISTING

```
<160> NUMBER OF SEQ ID NOS: 65

<210> SEQ ID NO 1
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (30)..(30)
<223> OTHER INFORMATION: The carboxy-terminal amino acid residue
      comprises a carboxyl group or one of the following groups: amido,
``` hydrophobic, macromolecular, t-butyloxycarbonyl, lipid,
polyethyleneglycol, or carbohydrate

<400> SEQUENCE: 1

Tyr Gln Val Arg Asn Ser Ser Gly Leu Tyr His Val Thr Asn Asp Cys
1               5                   10                  15

Pro Asn Ser Ser Ile Val Tyr Glu Ala Ala Asp Ala Ile Leu
            20                  25                  30

<210> SEQ ID NO 2
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (34)..(34)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 2

Cys Ser Ala Leu Tyr Trp Val Gly Asp Leu Cys Gly Ser Val Phe Leu
1               5                   10                  15

Val Gly Gln Leu Phe Thr Phe Ser Pro Arg Arg His Trp Thr Thr Gln
            20                  25                  30

Asp Cys

<210> SEQ ID NO 3
<211> LENGTH: 36
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (36)..(36)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 3

Ser Pro Arg Arg His Trp Thr Thr Gln Asp Cys Asn Cys Ser Ile Tyr
1               5                   10                  15

Pro Gly His Ile Thr Gly His Arg Met Ala Trp Asp Met Met Met Asn
            20                  25                  30

Trp Ser Pro Thr
        35

```
<210> SEQ ID NO 4
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (42)..(42)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 4

Met Met Met Asn Trp Ser Pro Thr Ala Ala Leu Leu Arg Ile Pro Gln
1               5                   10                  15

Ala Ile Met Asp Met Ile Ala Gly Ala His Trp Gly Val Leu Ala Gly
            20                  25                  30

Ile Lys Tyr Phe Ser Met Val Gly Asn Trp
        35                  40

<210> SEQ ID NO 5
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (30)..(30)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 5

Arg Val Thr Asp Pro Asp Thr Asn Thr Thr Ile Leu Thr Asn Cys Cys
1               5                   10                  15

Gln Arg Asn Gln Val Ile Tyr Cys Ser Pro Ser Thr Cys Leu
            20                  25                  30

<210> SEQ ID NO 6
<211> LENGTH: 35
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl, dansyl,
      t-butyloxycarbonyl, lipid, polyethylene glycol, or carbohydrate
<220> FEATURE:
```

```
<221> NAME/KEY: MOD_RES
<222> LOCATION: (35)..(35)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 6

Arg Asp Phe Val Glu Gly Val Ser Gly Ser Trp Val Asp Ile Val
1               5                  10                  15

Leu Glu His Gly Ser Cys Val Thr Thr Met Ala Lys Asn Lys Pro Thr
            20                  25                  30

Leu Asp Phe
        35

<210> SEQ ID NO 7
<211> LENGTH: 35
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (35)..(35)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 7

Arg Asp Phe Ile Glu Gly Ala Ser Gly Ala Thr Trp Val Asp Leu Val
1               5                  10                  15

Leu Glu Gly Asp Ser Cys Leu Thr Ile Met Ala Asn Asp Lys Pro Thr
            20                  25                  30

Leu Asp Val
        35

<210> SEQ ID NO 8
<211> LENGTH: 35
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (35)..(35)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 8

Arg Asp Phe Ile Glu Gly Val His Gly Gly Thr Trp Val Ser Ala Thr
1               5                  10                  15
```

-continued

Leu Glu Gln Asp Lys Cys Val Thr Val Met Ala Pro Asp Lys Pro Ser
                20                  25                  30

Leu Asp Ile
        35

<210> SEQ ID NO 9
<211> LENGTH: 35
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (35)..(35)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 9

Arg Asp Phe Leu Glu Gly Val Ser Gly Ala Thr Trp Val Asp Leu Val
1               5                   10                  15

Leu Glu Gly Asp Ser Cys Val Thr Ile Met Ser Lys Asp Lys Pro Thr
                20                  25                  30

Ile Asp Val
        35

<210> SEQ ID NO 10
<211> LENGTH: 35
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (35)..(35)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 10

Gly Gln Leu Ala Cys Lys Glu Asp Tyr Arg Tyr Ala Ile Ser Ser Thr
1               5                   10                  15

Asn Glu Ile Gly Leu Leu Gly Ala Gly Gly Leu Thr Thr Thr Trp Lys
                20                  25                  30

Glu Tyr Asn
        35

<210> SEQ ID NO 11
<211> LENGTH: 35
<212> TYPE: PRT

```
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (35)..(35)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 11

Gly His Leu Asp Cys Lys Pro Glu Phe Ser Tyr Ala Ile Ala Lys Asp
1               5                   10                  15

Glu Arg Ile Gly Gln Leu Gly Ala Glu Gly Leu Thr Thr Thr Trp Lys
            20                  25                  30

Glu Tyr Ser
        35

<210> SEQ ID NO 12
<211> LENGTH: 35
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (35)..(35)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 12

Gly Glu Phe Ala Cys Arg Glu Asp His Arg Tyr Ala Leu Ala Lys Thr
1               5                   10                  15

Lys Glu Ile Gly Pro Leu Gly Ala Glu Ser Leu Thr Thr Thr Trp Thr
            20                  25                  30

Asp Tyr Gln
        35

<210> SEQ ID NO 13
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
```

```
<220> FEATURE:
<221> NAME/KEY: MOD_RES
<222> LOCATION: (34)..(34)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 13

Thr Cys Asp Ala Leu Asp Ile Gly Glu Leu Cys Gly Ala Cys Val Leu
1               5                   10                  15

Val Gly Asp Trp Leu Val Arg His Trp Leu Ile His Ile Asp Leu Asn
                20                  25                  30

Glu Thr

<210> SEQ ID NO 14
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (34)..(34)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 14

Lys Arg Phe Val Cys Lys His Ser Met Val Asp Arg Gly Trp Gly Asn
1               5                   10                  15

Gly Cys Gly Leu Phe Gly Lys Gly Gly Ile Val Thr Cys Ala Met Phe
                20                  25                  30

Thr Cys

<210> SEQ ID NO 15
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (34)..(34)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 15

Ser Ser Tyr Val Cys Lys Gln Gly Phe Thr Asp Arg Gly Trp Gly Asn
1               5                   10                  15
```

```
Gly Cys Gly Leu Phe Gly Lys Gly Ser Ile Asp Thr Cys Ala Lys Phe
            20                  25                  30

Ser Cys

<210> SEQ ID NO 16
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (34)..(34)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 16

Gly Asp Asn Ala Cys Lys Arg Thr Tyr Ser Asp Arg Gly Trp Gly Asn
1               5                   10                  15

Gly Cys Gly Leu Phe Gly Lys Gly Ser Ile Val Ala Cys Ala Lys Phe
            20                  25                  30

Thr Cys

<210> SEQ ID NO 17
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (34)..(34)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 17

Pro Ala Phe Val Cys Arg Gln Gly Val Val Asp Arg Gly Trp Gly Asn
1               5                   10                  15

Gly Cys Gly Leu Phe Gly Lys Gly Ser Ile Asp Thr Cys Ala Lys Phe
            20                  25                  30

Ala Cys

<210> SEQ ID NO 18
<211> LENGTH: 34
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (34)..(34)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 18

Lys Gly Lys Tyr Asn Thr Thr Leu Leu Asn Gly Ser Ala Phe Tyr Leu
1               5                   10                  15

Val Cys Pro Ile Gly Trp Thr Gly Val Ile Glu Cys Thr Ala Val Ser
            20                  25                  30

Pro Thr

<210> SEQ ID NO 19
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (34)..(34)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 19

Arg Gly Lys Phe Asn Thr Thr Leu Leu Asn Gly Pro Ala Phe Gln Met
1               5                   10                  15

Val Cys Pro Ile Gly Trp Thr Gly Thr Val Ser Cys Thr Ser Phe Asn
            20                  25                  30

Met Asp

<210> SEQ ID NO 20
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (34)..(34)
<223> OTHER INFORMATION: The carboxy-terminal amino acid residue
      comprises a carboxyl group or one of the following groups: amido,
      hydrophobic, macromolecular, t-butyloxycarbonyl, lipid,
```

-continued polyethyleneglycol, or carbohydrate

<400> SEQUENCE: 20

Arg Gly Lys Tyr Asn Ala Thr Leu Leu Asn Gly Ser Ala Phe Gln Leu
1               5                   10                  15

Val Cys Pro Tyr Glu Trp Thr Gly Arg Val Glu Cys Thr Thr Ile Ser
            20                  25                  30

Lys Ser

<210> SEQ ID NO 21
<211> LENGTH: 36
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (36)..(36)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 21

Ile His Ile Asp Leu Asn Glu Thr Gly Thr Cys Tyr Leu Glu Val Pro
1               5                   10                  15

Thr Gly Ile Asp Pro Gly Phe Leu Gly Phe Ile Gly Trp Met Ala Gly
            20                  25                  30

Lys Val Glu Ala
        35

<210> SEQ ID NO 22
<211> LENGTH: 36
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (36)..(36)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 22

Met Val Leu Leu Gln Met Glu Asp Lys Ala Trp Leu Val His Arg Gln
1               5                   10                  15

Trp Phe Leu Asp Leu Pro Leu Pro Trp Leu Pro Gly Ala Asp Thr Gln
            20                  25                  30

Gly Ser Asn Trp
        35

```
<210> SEQ ID NO 23
<211> LENGTH: 36
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (36)..(36)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 23

Phe Tyr Val Met Thr Val Gly Ser Lys Ser Phe Leu Val His Arg Glu
1               5                   10                  15

Trp Phe His Asp Leu Ala Leu Pro Trp Thr Ser Pro Ser Ser Thr Ala
            20                  25                  30

Trp Arg Asn Arg
        35

<210> SEQ ID NO 24
<211> LENGTH: 36
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (36)..(36)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 24

Ser Tyr Ile Ala Glu Met Glu Thr Glu Ser Trp Ile Val Asp Arg Gln
1               5                   10                  15

Trp Ala Gln Asp Leu Thr Leu Pro Trp Gln Ser Gly Ser Gly Gly Val
            20                  25                  30

Trp Arg Glu Met
        35

<210> SEQ ID NO 25
<211> LENGTH: 36
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
```

```
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (36)..(36)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 25

Tyr Tyr Val Met Thr Val Gly Thr Lys Thr Phe Leu Val His Arg Glu
1               5                   10                  15

Trp Phe Met Asp Leu Asn Leu Pro Trp Ser Ser Ala Gly Ser Thr Val
            20                  25                  30

Trp Arg Asn Arg
        35

<210> SEQ ID NO 26
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (34)..(34)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 26

Thr Leu Arg Thr Glu Val Val Lys Thr Phe Arg Arg Asp Lys Pro Phe
1               5                   10                  15

Pro His Arg Met Asp Ala Val Thr Thr Val Glu Asn Glu Asp Leu
            20                  25                  30

Phe Tyr

<210> SEQ ID NO 27
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (34)..(34)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate
```

<400> SEQUENCE: 27

Thr Leu Ala Thr Glu Val Val Lys Ile Tyr Lys Arg Thr Lys Arg Phe
1               5                   10                  15

Arg Ser Gly Leu Val Ala Thr His Thr Thr Ile Tyr Glu Glu Asp Leu
            20                  25                  30

Tyr His

<210> SEQ ID NO 28
<211> LENGTH: 33
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (33)..(33)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 28

Thr Leu Ala Thr Thr Val Val Arg Thr Tyr Arg Arg Ser Lys Pro Phe
1               5                   10                  15

Pro His Arg Gln Gly Ala Ile Thr Gln Lys Asn Leu Gly Glu Asp Leu
            20                  25                  30

His

<210> SEQ ID NO 29
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (42)..(42)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 29

Trp Met Ala Gly Lys Val Glu Ala Val Ile Phe Leu Thr Lys Leu Ala
1               5                   10                  15

Ser Gln Val Pro Tyr Ala Ile Ala Thr Met Phe Ser Ser Val His Tyr
            20                  25                  30

Leu Ala Val Gly Ala Leu Ile Tyr Tyr Ser
            35                  40

```
<210> SEQ ID NO 30
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (42)..(42)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 30

Met Ala Ile Leu Gly Asp Thr Ala Trp Asp Phe Gly Ser Leu Gly Gly
1               5                   10                  15

Val Phe Thr Ser Ile Gly Lys Ala Leu His Gln Val Phe Gly Ala Ile
            20                  25                  30

Tyr Gly Ala Ala Phe Ser Gly Val Ser Trp
        35                  40

<210> SEQ ID NO 31
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (42)..(42)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 31

Leu Ala Ala Leu Gly Asp Thr Ala Trp Asp Phe Gly Ser Ile Gly Gly
1               5                   10                  15

Val Phe Asn Ser Ile Gly Lys Ala Val His Gln Val Phe Gly Gly Ala
            20                  25                  30

Phe Arg Thr Leu Phe Gly Gly Met Ser Trp
        35                  40

<210> SEQ ID NO 32
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
```

```
        groups: acetyl, hydrophobic, macromolecular, carbobenzoxyl,
        dansyl, t-butyloxycarbonyl, lipid, polyethylene glycol, or
        carbohydrate
<220> FEATURE:
<221> NAME/KEY: MOD_RES
<222> LOCATION: (42)..(42)
<223> OTHER INFORMATION: The carboxy-terminal amino acid residue
        comprises a carboxyl group or one of the following groups: amido,
        hydrophobic, macromolecular, t-butyloxycarbonyl, lipid,
        polyethyleneglycol, or carbohydrate

<400> SEQUENCE: 32

Leu Ala Val Met Gly Asp Thr Ala Trp Asp Phe Ser Ser Ala Gly Gly
1               5                   10                  15

Phe Phe Thr Ser Val Gly Lys Gly Ile His Thr Val Phe Gly Ser Ala
            20                  25                  30

Phe Gln Gly Leu Phe Gly Gly Leu Asn Trp
        35                  40

<210> SEQ ID NO 33
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
        an amino group or is modified to contain one of the following
        groups: acetyl, hydrophobic, macromolecular, carbobenzoxyl,
        dansyl, t-butyloxycarbonyl, lipid, polyethylene glycol, or
        carbohydrate
<220> FEATURE:
<221> NAME/KEY: MOD_RES
<222> LOCATION: (42)..(42)
<223> OTHER INFORMATION: The carboxy-terminal amino acid residue
        comprises a carboxyl group or one of the following groups: amido,
        hydrophobic, macromolecular, t-butyloxycarbonyl, lipid,
        polyethyleneglycol, or carbohydrate

<400> SEQUENCE: 33

Leu Ala Ala Leu Gly Asp Thr Ala Trp Asp Phe Gly Ser Val Gly Gly
1               5                   10                  15

Val Phe Thr Ser Val Gly Lys Ala Val His Gln Val Phe Gly Gly Ala
            20                  25                  30

Phe Arg Ser Leu Phe Gly Gly Met Ser Trp
        35                  40

<210> SEQ ID NO 34
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
        an amino group or is modified to contain one of the following
        groups: acetyl, hydrophobic, macromolecular, carbobenzoxyl,
        dansyl, t-butyloxycarbonyl, lipid, polyethylene glycol, or
        carbohydrate
<220> FEATURE:
<221> NAME/KEY: MOD_RES
<222> LOCATION: (42)..(42)
<223> OTHER INFORMATION: The carboxy-terminal amino acid residue
        comprises a carboxyl group or one of the following groups: amido,
        hydrophobic, macromolecular, t-butyloxycarbonyl, lipid,
        polyethyleneglycol, or carbohydrate
```

```
<400> SEQUENCE: 34

Gln Gln Tyr Met Leu Lys Gly Glu Tyr Gln Tyr Trp Phe Asp Leu Asp
1               5                   10                  15

Val Thr Asp Arg His Ser Asp Tyr Phe Ala Glu Phe Val Val Leu Val
            20                  25                  30

Val Val Ala Leu Leu Gly Gly Arg Tyr Ile
        35                  40

<210> SEQ ID NO 35
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (42)..(42)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 35

Gln Gln Tyr Met Leu Lys Gly Glu Tyr Gln Tyr Trp Phe Asp Leu Glu
1               5                   10                  15

Val Thr Asp His His Arg Asp Tyr Phe Ala Glu Ser Ile Leu Val Val
            20                  25                  30

Val Val Ala Leu Leu Gly Gly Arg Tyr Val
        35                  40

<210> SEQ ID NO 36
<211> LENGTH: 43
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: The amino-terminal amino acid residue comprises
      an amino group or is modified to contain one of the following
      groups: acetyl, hydrophobic, macromolecular, carbobenzoxyl,
      dansyl, t-butyloxycarbonyl, lipid, polyethylene glycol, or
      carbohydrate
<220> FEATURE:
<221> NAME/KEY: MOD_RES
<222> LOCATION: (43)..(43)
<223> OTHER INFORMATION: The carboxy-terminal amino acid residue
      comprises a carboxyl group or one of the following groups: amido,
      hydrophobic, macromolecular, t-butyloxycarbonyl, lipid,
      polyethyleneglycol, or carbohydrate

<400> SEQUENCE: 36

Gln Gln Tyr Met Leu Lys Gly Gln Tyr Gln Tyr Trp Phe Asp Leu Glu
1               5                   10                  15

Val Ile Ser Ser Thr His Gln Ile Asp Leu Thr Glu Phe Ile Met Leu
            20                  25                  30

Ala Val Val Ala Leu Leu Gly Gly Arg Tyr Val
        35                  40
```

```
<210> SEQ ID NO 37
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 37

Arg Xaa Arg Lys Arg
1               5

<210> SEQ ID NO 38
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 38

Ser Cys Leu Thr Val Pro Ala Ser Ala Tyr Gln Val Arg Asn Ser Ser
1               5                   10                  15

Gly Leu

<210> SEQ ID NO 39
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 39

Ser Ala Tyr Gln Val Arg Asn Ser Ser Gly Leu Tyr His Val Thr Asn
1               5                   10                  15

Asp Cys

<210> SEQ ID NO 40
<211> LENGTH: 18
<212> TYPE: PRT
<213> ORGANISM: Artificial Sequence
<220> FEATURE:
<223> OTHER INFORMATION: Synthetic peptide

<400> SEQUENCE: 40

Ser Ser Gly Leu Tyr His Val Thr Asn Asp Cys Pro Asn Ser Ser Ile
1               5                   10                  15

Val Tyr

<210> SEQ ID NO 41
<211> LENGTH: 18
<212> TYPE: PRT
<213> ORGANISM: Artificial Sequence
<220> FEATURE:
<223> OTHER INFORMATION: Synthetic peptide

<400> SEQUENCE: 41

Thr Asn Asp Cys Pro Asn Ser Ser Val Val Tyr Glu Ala Ala Asp Ala
1               5                   10                  15

Ile Leu

<210> SEQ ID NO 42
```

```
<211> LENGTH: 18
<212> TYPE: PRT
<213> ORGANISM: Artificial Sequence
<220> FEATURE:
<223> OTHER INFORMATION: Synthetic peptide

<400> SEQUENCE: 42

Ser Ile Val Tyr Glu Ala Ala Asp Ala Ile Leu His Thr Pro Gly Cys
1               5                   10                  15

Val Pro

<210> SEQ ID NO 43
<211> LENGTH: 18
<212> TYPE: PRT
<213> ORGANISM: Artificial Sequence
<220> FEATURE:
<223> OTHER INFORMATION: Synthetic peptide

<400> SEQUENCE: 43

Asp Ala Ile Leu His Thr Pro Gly Cys Val Pro Cys Val Arg Glu Gly
1               5                   10                  15

Asn Ala

<210> SEQ ID NO 44
<211> LENGTH: 18
<212> TYPE: PRT
<213> ORGANISM: Artificial Sequence
<220> FEATURE:
<223> OTHER INFORMATION: Synthetic peptide

<400> SEQUENCE: 44

Gly Cys Val Pro Cys Val Arg Glu Gly Asn Ala Ser Arg Cys Trp Val
1               5                   10                  15

Ala Val

<210> SEQ ID NO 45
<211> LENGTH: 18
<212> TYPE: PRT
<213> ORGANISM: Artificial Sequence
<220> FEATURE:
<223> OTHER INFORMATION: Synthetic peptide

<400> SEQUENCE: 45

Trp Val Ala Val Thr Pro Thr Val Ala Thr Arg Asp Gly Lys Leu Pro
1               5                   10                  15

Thr Thr

<210> SEQ ID NO 46
<211> LENGTH: 18
<212> TYPE: PRT
<213> ORGANISM: Artificial Sequence
<220> FEATURE:
<223> OTHER INFORMATION: Synthetic peptide

<400> SEQUENCE: 46

Trp Val Ala Val Thr Pro Thr Val Ala Thr Arg Asp Gly Lys Leu Pro
1               5                   10                  15

Thr Thr

<210> SEQ ID NO 47
<211> LENGTH: 18
<212> TYPE: PRT
<213> ORGANISM: Artificial Sequence
<220> FEATURE:
```

-continued

<223> OTHER INFORMATION: Synthetic peptide

<400> SEQUENCE: 47

Val Ala Thr Arg Asp Gly Lys Leu Pro Thr Thr Gln Leu Arg Arg His
1               5                   10                  15

Ile Asp

<210> SEQ ID NO 48
<211> LENGTH: 18
<212> TYPE: PRT
<213> ORGANISM: Artificial Sequence
<220> FEATURE:
<223> OTHER INFORMATION: Synthetic peptide

<400> SEQUENCE: 48

Leu Pro Thr Thr Gln Leu Arg Arg His Ile Asp Leu Leu Val Gly Ser
1               5                   10                  15

Ala Thr

<210> SEQ ID NO 49
<211> LENGTH: 18
<212> TYPE: PRT
<213> ORGANISM: Artificial Sequence
<220> FEATURE:
<223> OTHER INFORMATION: Synthetic peptide

<400> SEQUENCE: 49

Arg His Ile Asp Leu Leu Val Gly Ser Ala Thr Leu Cys Ser Ala Leu
1               5                   10                  15

Tyr Val

<210> SEQ ID NO 50
<211> LENGTH: 18
<212> TYPE: PRT
<213> ORGANISM: Artificial Sequence
<220> FEATURE:
<223> OTHER INFORMATION: Synthetic peptide

<400> SEQUENCE: 50

Gly Ser Ala Thr Leu Cys Ser Ala Leu Tyr Val Gly Asp Leu Cys Gly
1               5                   10                  15

Ser Val

<210> SEQ ID NO 51
<211> LENGTH: 18
<212> TYPE: PRT
<213> ORGANISM: Artificial Sequence
<220> FEATURE:
<223> OTHER INFORMATION: Synthetic peptide

<400> SEQUENCE: 51

Ala Leu Tyr Val Gly Asp Leu Cys Gly Ser Val Phe Leu Val Gly Gln
1               5                   10                  15

Leu Phe

<210> SEQ ID NO 52
<211> LENGTH: 18
<212> TYPE: PRT
<213> ORGANISM: Artificial Sequence
<220> FEATURE:
<223> OTHER INFORMATION: Synthetic peptide

<400> SEQUENCE: 52

```
Cys Gly Ser Val Phe Leu Val Gly Gln Leu Phe Thr Phe Ser Pro Arg
1               5                   10                  15

His His
```

<210> SEQ ID NO 53
<211> LENGTH: 18
<212> TYPE: PRT
<213> ORGANISM: Artificial Sequence
<220> FEATURE:
<223> OTHER INFORMATION: Synthetic peptide

<400> SEQUENCE: 53

```
Gly Gln Leu Phe Thr Phe Ser Pro Arg His His Trp Thr Thr Gln Asp
1               5                   10                  15

Cys Asn
```

<210> SEQ ID NO 54
<211> LENGTH: 18
<212> TYPE: PRT
<213> ORGANISM: Artificial Sequence
<220> FEATURE:
<223> OTHER INFORMATION: Synthetic peptide

<400> SEQUENCE: 54

```
Pro Arg His His Trp Thr Thr Gln Asp Cys Asn Cys Ser Ile Tyr Pro
1               5                   10                  15

Gly His
```

<210> SEQ ID NO 55
<211> LENGTH: 18
<212> TYPE: PRT
<213> ORGANISM: Artificial Sequence
<220> FEATURE:
<223> OTHER INFORMATION: Synthetic peptide

<400> SEQUENCE: 55

```
Gln Asp Cys Asn Cys Ser Ile Tyr Pro Gly His Ile Thr Gly His Arg
1               5                   10                  15

Met Ala
```

<210> SEQ ID NO 56
<211> LENGTH: 17
<212> TYPE: PRT
<213> ORGANISM: Artificial Sequence
<220> FEATURE:
<223> OTHER INFORMATION: Synthetic peptide

<400> SEQUENCE: 56

```
Tyr Pro Gly His Ile Thr Gly His Arg Met Ala Asn Met Met Met Asn
1               5                   10                  15

Trp
```

<210> SEQ ID NO 57
<211> LENGTH: 17
<212> TYPE: PRT
<213> ORGANISM: Artificial Sequence
<220> FEATURE:
<223> OTHER INFORMATION: Synthetic peptide

<400> SEQUENCE: 57

```
His Arg Met Ala Asn Met Met Met Asn Trp Ser Pro Thr Ala Ala Leu
1               5                   10                  15

Val
```

<210> SEQ ID NO 58
<211> LENGTH: 18
<212> TYPE: PRT
<213> ORGANISM: Artificial Sequence
<220> FEATURE:
<223> OTHER INFORMATION: Synthetic peptide

<400> SEQUENCE: 58

Met Met Asn Trp Ser Pro Thr Ala Ala Leu Val Val Ala Gln Leu Leu
1               5                   10                  15

Arg Ile

<210> SEQ ID NO 59
<211> LENGTH: 18
<212> TYPE: PRT
<213> ORGANISM: Artificial Sequence
<220> FEATURE:
<223> OTHER INFORMATION: Synthetic peptide

<400> SEQUENCE: 59

Ala Ala Leu Val Val Ala Gln Leu Leu Arg Ile Pro Gln Ala Ile Met
1               5                   10                  15

Asp Met

<210> SEQ ID NO 60
<211> LENGTH: 18
<212> TYPE: PRT
<213> ORGANISM: Artificial Sequence
<220> FEATURE:
<223> OTHER INFORMATION: Synthetic peptide

<400> SEQUENCE: 60

Leu Leu Arg Ile Pro Gln Ala Ile Met Asp Met Ile Ala Gly Ala His
1               5                   10                  15

Trp Gly

<210> SEQ ID NO 61
<211> LENGTH: 18
<212> TYPE: PRT
<213> ORGANISM: Artificial Sequence
<220> FEATURE:
<223> OTHER INFORMATION: Synthetic peptide

<400> SEQUENCE: 61

Ile Met Asp Met Ile Ala Gly Ala His Trp Gly Val Leu Ala Gly Ile
1               5                   10                  15

Lys Tyr

<210> SEQ ID NO 62
<211> LENGTH: 18
<212> TYPE: PRT
<213> ORGANISM: Artificial Sequence
<220> FEATURE:
<223> OTHER INFORMATION: Synthetic peptide

<400> SEQUENCE: 62

Ala His Trp Gly Val Leu Ala Gly Ile Lys Tyr Phe Ser Met Val Gly
1               5                   10                  15

Asn Trp

<210> SEQ ID NO 63
<211> LENGTH: 18

```
<212> TYPE: PRT
<213> ORGANISM: Artificial Sequence
<220> FEATURE:
<223> OTHER INFORMATION: Synthetic peptide

<400> SEQUENCE: 63

Gly Ile Lys Tyr Phe Ser Met Val Gly Asn Trp Ala Lys Val Leu Val
1               5                   10                  15

Val Leu

<210> SEQ ID NO 64
<211> LENGTH: 18
<212> TYPE: PRT
<213> ORGANISM: Artificial Sequence
<220> FEATURE:
<223> OTHER INFORMATION: Synthetic peptide

<400> SEQUENCE: 64

Val Gly Asn Trp Ala Lys Val Leu Val Val Leu Leu Leu Phe Ala Gly
1               5                   10                  15

Val Asp

<210> SEQ ID NO 65
<211> LENGTH: 18
<212> TYPE: PRT
<213> ORGANISM: Artificial Sequence
<220> FEATURE:
<223> OTHER INFORMATION: Synthetic peptide

<400> SEQUENCE: 65

Leu Val Val Leu Leu Leu Phe Ala Gly Val Asp Ala Glu Thr His Val
1               5                   10                  15

Thr Gly
```